(12) United States Patent
Saadat et al.

(10) Patent No.: US 11,369,356 B2
(45) Date of Patent: Jun. 28, 2022

(54) METHODS AND APPARATUS FOR PREVENTING TISSUE MIGRATION

(71) Applicant: INTUITIVE SURGICAL OPERATIONS, INC., Sunnyvale, CA (US)

(72) Inventors: Vahid Saadat, Atherton, CA (US); Ruey-Feng Peh, Singapore (SG); Christopher A. Rothe, San Mateo, CA (US); Edmund A. Tam, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 16/413,328

(22) Filed: May 15, 2019

(65) Prior Publication Data

US 2019/0314007 A1    Oct. 17, 2019

Related U.S. Application Data

(62) Division of application No. 11/877,386, filed on Oct. 23, 2007, now Pat. No. 10,335,131.
(Continued)

(51) Int. Cl.
*A61B 1/00*     (2006.01)
*A61B 17/02*    (2006.01)
(Continued)

(52) U.S. Cl.
CPC .......... *A61B 17/02* (2013.01); *A61B 1/00089* (2013.01); *A61B 1/3137* (2013.01);
(Continued)

(58) Field of Classification Search
CPC ............ A61B 1/00073; A61B 1/00075; A61B 1/00087; A61B 1/3137; A61B 17/02; A61M 2025/0092; A61M 2025/0087
(Continued)

(56) References Cited

U.S. PATENT DOCUMENTS 623,022 A    4/1899   Johnson
2,305,462 A  12/1942  Wolf
(Continued)

FOREIGN PATENT DOCUMENTS

DE    10028155 A1   12/2000
EP    0283661 A2    9/1988
(Continued)

OTHER PUBLICATIONS

Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.
(Continued)

*Primary Examiner* — Alexandra L Newton
*Assistant Examiner* — Rynae E Boler
(74) *Attorney, Agent, or Firm* — Haynes and Boone, LLP

(57) ABSTRACT

An apparatus for inhibiting tissue migration during a procedure comprises a deployment catheter defining at least one lumen therethrough and a non-inflatable hood projecting distally from the deployment catheter and defining an open area. The open area is in fluid communication with the at least one lumen. The apparatus also comprises a visualization element disposed within or along the non-inflatable hood for visualizing tissue adjacent to the open area. The apparatus also comprises a tissue grasping end effector positioned within the open area and configured to temporarily engage the tissue adjacent to the open area such that
(Continued)

distal migration of the tissue relative to the barrier or membrane is inhibited.

7 Claims, 34 Drawing Sheets

Related U.S. Application Data

(60) Provisional application No. 60/862,575, filed on Oct. 23, 2006.

(51) Int. Cl.
*A61B 1/313* (2006.01)
*A61B 17/34* (2006.01)
*A61B 1/005* (2006.01)
*A61B 6/00* (2006.01)
*A61B 8/08* (2006.01)

(52) U.S. Cl.
CPC .......... *A61B 17/3439* (2013.01); *A61B 1/005* (2013.01); *A61B 6/503* (2013.01); *A61B 8/0883* (2013.01); *A61B 2017/0237* (2013.01)

(58) Field of Classification Search
USPC .......................................... 600/104, 115, 116
See application file for complete search history.

(56) References Cited

U.S. PATENT DOCUMENTS

| | | |
|---|---|---|
| 2,453,862 A | 11/1948 | Salisbury |
| 3,559,651 A | 2/1971 | David |
| 3,874,388 A | 4/1975 | King et al. |
| 4,175,545 A | 11/1979 | Termanini |
| 4,326,529 A | 4/1982 | Doss et al. |
| 4,445,892 A | 5/1984 | Hussein et al. |
| 4,470,407 A | 9/1984 | Hussein |
| 4,517,976 A | 5/1985 | Murakoshi et al. |
| 4,569,335 A | 2/1986 | Tsuno |
| 4,576,146 A | 3/1986 | Kawazoe et al. |
| 4,615,333 A | 10/1986 | Taguchi |
| 4,619,247 A | 10/1986 | Inoue et al. |
| 4,676,258 A | 6/1987 | Inokuchi et al. |
| 4,681,093 A | 7/1987 | Ono et al. |
| 4,709,698 A | 12/1987 | Johnston et al. |
| 4,710,192 A | 12/1987 | Liotta et al. |
| 4,727,418 A | 2/1988 | Kato et al. |
| 4,784,133 A | 11/1988 | Mackin |
| 4,848,323 A | 7/1989 | Marijnissen et al. |
| 4,911,148 A | 3/1990 | Sosnowski et al. |
| 4,914,521 A | 4/1990 | Adair |
| 4,943,290 A | 7/1990 | Rexroth et al. |
| 4,950,285 A | 8/1990 | Wilk |
| 4,957,484 A | 9/1990 | Murtfeldt |
| 4,961,738 A | 10/1990 | Mackin |
| 4,976,710 A | 12/1990 | Mackin |
| 4,991,578 A | 2/1991 | Cohen |
| 4,994,069 A | 2/1991 | Ritchart et al. |
| 4,998,916 A | 3/1991 | Hammerslag et al. |
| 4,998,972 A | 3/1991 | Chin et al. |
| 5,047,028 A | 9/1991 | Qian |
| 5,057,106 A | 10/1991 | Kasevich et al. |
| 5,090,959 A | 2/1992 | Samson et al. |
| 5,123,428 A | 6/1992 | Schwarz |
| RE34,002 E | 7/1992 | Adair |
| 5,156,141 A | 10/1992 | Krebs et al. |
| 5,171,259 A | 12/1992 | Inoue |
| 5,254,129 A | 10/1993 | Alexander |
| 5,281,238 A | 1/1994 | Chin et al. |
| 5,282,827 A | 2/1994 | Kensey et al. |
| 5,306,234 A | 4/1994 | Johnson |
| 5,312,417 A | 5/1994 | Wilk |
| 5,313,943 A | 5/1994 | Houser et al. |
| 5,330,496 A | 7/1994 | Alferness |
| 5,334,159 A | 8/1994 | Turkel |
| 5,334,193 A | 8/1994 | Nardella |
| 5,336,252 A | 8/1994 | Cohen |
| 5,339,800 A | 8/1994 | Wiita et al. |
| 5,348,554 A | 9/1994 | Imran et al. |
| 5,353,792 A | 10/1994 | Luebbers et al. |
| 5,370,647 A | 12/1994 | Graber et al. |
| 5,373,840 A | 12/1994 | Knighton |
| 5,375,612 A | 12/1994 | Cottenceau et al. |
| 5,385,148 A | 1/1995 | Lesh et al. |
| 5,391,182 A | 2/1995 | Chin |
| 5,403,326 A | 4/1995 | Harrison et al. |
| 5,421,338 A | 6/1995 | Crowley et al. |
| 5,431,649 A | 7/1995 | Mulier et al. |
| 5,453,785 A | 9/1995 | Lenhardt et al. |
| 5,462,521 A | 10/1995 | Brucker et al. |
| 5,471,515 A | 11/1995 | Fossum et al. |
| 5,498,230 A | 3/1996 | Adair |
| 5,505,730 A | 4/1996 | Edwards |
| 5,515,853 A | 5/1996 | Smith et al. |
| 5,527,338 A | 6/1996 | Purdy |
| 5,549,603 A | 8/1996 | Feiring |
| 5,558,619 A | 9/1996 | Kami et al. |
| 5,571,088 A | 11/1996 | Lennox et al. |
| 5,575,756 A | 11/1996 | Karasawa et al. |
| 5,575,810 A | 11/1996 | Swanson et al. |
| 5,584,872 A | 12/1996 | Lafontaine et al. |
| 5,591,119 A | 1/1997 | Adair |
| 5,593,405 A | 1/1997 | Osypka |
| 5,593,422 A | 1/1997 | Muijs et al. |
| 5,593,424 A | 1/1997 | Northrup, III |
| 5,672,153 A | 9/1997 | Lax et al. |
| 5,676,693 A | 10/1997 | Lafontaine |
| 5,681,308 A | 10/1997 | Edwards et al. |
| 5,695,448 A | 12/1997 | Kimura et al. |
| 5,697,281 A | 12/1997 | Eggers et al. |
| 5,697,882 A | 12/1997 | Eggers et al. |
| 5,709,224 A | 1/1998 | Behl et al. |
| 5,713,907 A | 2/1998 | Hogendijk et al. |
| 5,713,946 A | 2/1998 | Ben-Haim |
| 5,716,321 A | 2/1998 | Kerin et al. |
| 5,722,403 A | 3/1998 | McGee et al. |
| 5,725,523 A | 3/1998 | Mueller |
| 5,746,747 A | 5/1998 | McKeating |
| 5,749,846 A | 5/1998 | Edwards et al. |
| 5,749,890 A | 5/1998 | Shaknovich |
| 5,754,313 A | 5/1998 | Pelchy et al. |
| 5,766,137 A | 6/1998 | Omata |
| 5,769,846 A | 6/1998 | Edwards et al. |
| 5,792,045 A | 8/1998 | Adair |
| 5,797,903 A | 8/1998 | Swanson et al. |
| 5,823,947 A | 10/1998 | Yoon et al. |
| 5,827,268 A | 10/1998 | Laufer |
| 5,829,447 A | 11/1998 | Stevens et al. |
| 5,842,973 A | 12/1998 | Bullard |
| 5,843,118 A | 12/1998 | Sepetka et al. |
| 5,848,969 A | 12/1998 | Panescu et al. |
| 5,860,974 A | 1/1999 | Abele |
| 5,860,991 A | 1/1999 | Klein et al. |
| 5,865,791 A | 2/1999 | Whayne et al. |
| 5,873,815 A | 2/1999 | Kerin et al. |
| 5,879,366 A | 3/1999 | Shaw et al. |
| 5,895,417 A | 4/1999 | Pomeranz et al. |
| 5,897,487 A | 4/1999 | Ouchi |
| 5,897,553 A | 4/1999 | Mulier et al. |
| 5,902,328 A | 5/1999 | Lafontaine et al. |
| 5,904,651 A | 5/1999 | Swanson et al. |
| 5,908,445 A | 6/1999 | Whayne et al. |
| 5,925,038 A | 7/1999 | Panescu et al. |
| 5,928,250 A | 7/1999 | Koike et al. |
| 5,929,901 A | 7/1999 | Adair et al. |
| 5,941,845 A | 8/1999 | Tu et al. |
| 5,944,690 A | 8/1999 | Falwell et al. |
| 5,964,755 A | 10/1999 | Edwards |
| 5,968,053 A | 10/1999 | Revelas |
| 5,971,983 A | 10/1999 | Lesh |
| 5,986,693 A | 11/1999 | Adair et al. |
| 5,997,571 A | 12/1999 | Farr et al. |
| 6,004,269 A | 12/1999 | Crowley et al. |

(56) References Cited

U.S. PATENT DOCUMENTS

| | | | |
|---|---|---|---|
| 6,012,457 A | 1/2000 | Lesh | |
| 6,024,740 A | 2/2000 | Lesh et al. | |
| 6,027,501 A | 2/2000 | Goble et al. | |
| 6,036,685 A | 3/2000 | Mueller | |
| 6,043,839 A | 3/2000 | Adair et al. | |
| 6,047,218 A | 4/2000 | Whayne et al. | |
| 6,063,077 A | 5/2000 | Schaer | |
| 6,063,081 A | 5/2000 | Mulier et al. | |
| 6,068,653 A | 5/2000 | Lafontaine | |
| 6,071,279 A | 6/2000 | Whayne et al. | |
| 6,071,302 A | 6/2000 | Sinofsky et al. | |
| 6,081,740 A | 6/2000 | Gombrich et al. | |
| 6,086,528 A | 7/2000 | Adair | |
| 6,099,498 A | 8/2000 | Addis | |
| 6,099,514 A | 8/2000 | Sharkey et al. | |
| 6,102,905 A | 8/2000 | Baxter et al. | |
| 6,115,626 A | 9/2000 | Whayne et al. | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,165,188 A * | 12/2000 | Saadat | A61B 17/3207 604/22 |
| 6,167,297 A | 12/2000 | Benaron | |
| 6,168,591 B1 | 1/2001 | Sinofsky | |
| 6,168,594 B1 | 1/2001 | Lafontaine et al. | |
| 6,174,307 B1 | 1/2001 | Daniel et al. | |
| 6,178,346 B1 | 1/2001 | Amundson et al. | |
| 6,190,381 B1 | 2/2001 | Olsen et al. | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,263,224 B1 | 7/2001 | West | |
| 6,270,492 B1 | 8/2001 | Sinofsky | |
| 6,275,255 B1 | 8/2001 | Adair et al. | |
| 6,290,689 B1 | 9/2001 | Delaney et al. | |
| 6,306,081 B1 | 10/2001 | Ishikawa et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 | 11/2001 | Gambale et al. | |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 | 6/2002 | Farley et al. | |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,440,061 B1 | 8/2002 | Wenner et al. | |
| 6,440,119 B1 | 8/2002 | Nakada et al. | |
| 6,458,151 B1 | 10/2002 | Saltiel | |
| 6,464,697 B1 | 10/2002 | Edwards et al. | |
| 6,474,340 B1 | 11/2002 | Vaska et al. | |
| 6,475,223 B1 | 11/2002 | Werp et al. | |
| 6,478,769 B1 | 11/2002 | Parker | |
| 6,482,162 B1 | 11/2002 | Moore | |
| 6,484,727 B1 | 11/2002 | Vaska et al. | |
| 6,485,489 B2 | 11/2002 | Teirstein et al. | |
| 6,488,671 B1 | 12/2002 | Constantz et al. | |
| 6,494,902 B2 | 12/2002 | Hoey et al. | |
| 6,497,705 B2 | 12/2002 | Comben | |
| 6,500,174 B1 | 12/2002 | Maguire et al. | |
| 6,502,576 B1 | 1/2003 | Lesh | |
| 6,514,249 B1 | 2/2003 | Maguire et al. | |
| 6,517,533 B1 | 2/2003 | Swaminathan | |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 | 4/2003 | Hassett et al. | |
| 6,544,195 B2 | 4/2003 | Wilson et al. | |
| 6,547,780 B1 | 4/2003 | Sinofsky | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,572,609 B1 | 6/2003 | Farr et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 | 8/2003 | Sinofsky et al. | |
| 6,613,062 B1 | 9/2003 | Leckrone et al. | |
| 6,622,732 B2 | 9/2003 | Constantz | |
| 6,626,855 B1 | 9/2003 | Weng et al. | |
| 6,626,900 B1 | 9/2003 | Sinofsky et al. | |
| 6,635,070 B2 | 10/2003 | Leeflang et al. | |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. et al. | |
| 6,682,526 B1 | 1/2004 | Jones et al. | |
| 6,689,128 B2 | 2/2004 | Sliwa et al. | |
| 6,692,430 B2 | 2/2004 | Adler | |
| 6,701,581 B2 | 3/2004 | Senovich et al. | |
| 6,701,931 B2 | 3/2004 | Sliwa et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa et al. | |
| 6,730,063 B2 | 5/2004 | Delaney et al. | |
| 6,736,810 B2 | 5/2004 | Hoey et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa et al. | |
| 6,849,073 B2 | 2/2005 | Hoey et al. | |
| 6,858,005 B2 | 2/2005 | Ohline et al. | |
| 6,858,026 B2 | 2/2005 | Sliwa et al. | |
| 6,863,668 B2 | 3/2005 | Gillespie et al. | |
| 6,866,651 B2 | 3/2005 | Constantz | |
| 6,887,237 B2 | 5/2005 | McGaffigan | |

(56) References Cited

U.S. PATENT DOCUMENTS

| | | |
|---|---|---|
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | Lafontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,736,347 B2 | 6/2010 | Kaplan et al. |
| 7,758,499 B2 | 7/2010 | Adler |
| 7,860,555 B2 * | 12/2010 | Saadat ............... A61B 1/0008 600/476 |
| 7,860,556 B2 | 12/2010 | Saadat |
| 7,930,016 B1 * | 4/2011 | Saadat ............... A61B 1/0008 600/101 |
| 8,012,151 B1 * | 9/2011 | Laufer ............... A61B 18/1492 606/151 |
| 8,131,350 B2 | 3/2012 | Saadat et al. |
| 8,137,333 B2 | 3/2012 | Saadat et al. |
| 10,335,131 B2 | 7/2019 | Saadat et al. |
| 2001/0020126 A1 | 9/2001 | Swanson et al. |
| 2001/0047136 A1 | 11/2001 | Domanik et al. |
| 2001/0047184 A1 | 11/2001 | Connors |
| 2002/0004644 A1 | 1/2002 | Koblish |
| 2002/0026145 A1 | 2/2002 | Bagaoisan et al. |
| 2002/0040226 A1 * | 4/2002 | Laufer ............... A61B 17/0057 606/153 |
| 2002/0054852 A1 | 5/2002 | Cate |
| 2002/0065455 A1 | 5/2002 | Ben-Haim et al. |
| 2002/0077687 A1 * | 6/2002 | Ahn ............... A61M 25/0084 607/120 |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0165598 A1 | 11/2002 | Wahr et al. |
| 2002/0169377 A1 * | 11/2002 | Khairkhahan ... A61B 17/32075 600/433 |
| 2003/0009085 A1 | 1/2003 | Arai et al. |
| 2003/0035156 A1 | 2/2003 | Cooper |
| 2003/0055442 A1 | 3/2003 | Laufer et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0220574 A1 | 11/2003 | Markus et al. |
| 2003/0222325 A1 | 12/2003 | Jacobsen et al. |
| 2004/0010231 A1 * | 1/2004 | Leonhardt ......... A61M 25/0068 604/170.03 |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215180 A1 | 10/2004 | Starkebaum et al. |
| 2004/0220471 A1 | 11/2004 | Schwartz |
| 2004/0230131 A1 | 11/2004 | Kassab et al. |
| 2004/0242960 A1 | 12/2004 | Orban et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0119523 A1 * | 6/2005 | Starksen ............ A61B 17/00234 600/109 |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222557 A1 | 10/2005 | Baxter et al. |
| 2005/0222558 A1 | 10/2005 | Baxter et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |

(56) References Cited

U.S. PATENT DOCUMENTS

| | | |
|---|---|---|
| 2006/0069303 A1 | 3/2006 | Couvillon, Jr. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima et al. |
| 2006/0217755 A1 | 9/2006 | Eversull et al. |
| 2006/0224167 A1 | 10/2006 | Weisenburgh, II et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0135826 A1 | 6/2007 | Zaver et al. |
| 2007/0167801 A1 | 7/2007 | Webler et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015445 A1 | 1/2008 | Saadat et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0188759 A1 | 8/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0082623 A1 | 3/2009 | Rothe et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0203962 A1 | 8/2009 | Miller et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0275799 A1 | 11/2009 | Saadat et al. |
| 2009/0299363 A1 | 12/2009 | Saadat et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0010311 A1 | 1/2010 | Miller et al. |
| 2010/0094081 A1 | 4/2010 | Rothe et al. |
| 2010/0130836 A1 | 5/2010 | Malchano et al. |
| 2011/0060227 A1 | 3/2011 | Saadat |
| 2011/0060298 A1 | 3/2011 | Saadat |
| 2011/0144576 A1 | 6/2011 | Rothe et al. |
| 2012/0016221 A1 | 1/2012 | Saadat et al. |
| 2012/0059366 A1 | 3/2012 | Drews et al. |
| 2012/0150046 A1 | 6/2012 | Watson et al. |

FOREIGN PATENT DOCUMENTS

| | | |
|---|---|---|
| EP | 0301288 A1 | 2/1989 |
| JP | S5993413 A | 5/1984 |
| JP | S59181315 A | 10/1984 |
| JP | H01221133 A | 9/1989 |
| JP | H03284265 A | 12/1991 |
| JP | H05103746 A | 4/1993 |
| JP | H0951897 A | 2/1997 |
| JP | H11299725 A | 11/1999 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9818388 A1 | 5/1998 |
| WO | WO-03039350 A2 | 5/2003 |
| WO | WO-03053491 A2 | 7/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |
| WO | WO-2006091597 A1 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Hoey M.F., et al., "Intramural Ablation Using Radiofrequency Energy via Screw-Tip Catheter and Saline Electrode," Pacing and Clinical Electrophysiology, 1995, vol. 18, Part II, 487.

Huang, "Increase in the Lesion Size and Decrease in the Impedance Rise with a Saline Infusion Electrode Catheter for Radiofrequency," Circulation, 1989, vol. 80 (4), II-324.

Moser K.M ., et al., "Angioscopic Visualization of Pulmonary Emboli," Chest, 1980, vol. 77 (2), pp. 198-201.

Nakamura F., et al., "Percutaneous Intracardiac Surgery With Cardioscopic Guidance," SPIE, 1992, vol. 1642, pp. 214-216.

Pappone C., et al., "Circumferential Radiofrequency Ablation of Pulmonary Vein Ostia," Circulation, 2000, vol. 102, pp. 2619-2628.

Sethi K.K., et al., "Transseptal catheterization for the electrophysiologist: modification with a 'view'," Journal of Interventional Cardiac Electrophysiology, 2001, vol. 5 (1), pp. 97-99.

Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.

(56) References Cited

OTHER PUBLICATIONS

Willkampf F.H., et al., "Radiofrequency Ablation with a Cooled Porous Electrode Catheter," JACC, Abstract, 1988, vol. 11 (2), pp. 17A.
Avitall B., et al., "Right-Sided Driven Atrial Fibrillation in a Sterile Pericarditis Dog Model," Pacing and Clinical Electrophysiology, 1994, vol. 17, pp. 774.
Avitall, et al. "A Catheter System to Ablate Atrial Fibrillation in a Sterile Pericarditis Dog Model," Pacing and Clinical Electrophysiology, 1994, vol. 17, pp. 774.
Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.
Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.
Bhakta D., et al., "Principles of Electroanatomic Mapping," Indian Pacing and Electrophysiology Journal, 2008, vol. 8 (1), pp. 32-50.
Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010], Retrieved from the Internet:< URL: http://www.ncbi.nlm.nih.gov/sites/entrez>.
Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.
Communication from the Examining Division for Application No. EP06734083.6 dated Nov. 12, 2010, 3 pages.
Communication from the Examining Division for Application No. EP06734083.6 dated Oct. 23, 2009, 1 page.
Communication from the Examining Division for Application No. EP08746822.9 dated Jul. 13, 2010, 1 page.
Co-pending U.S. Appl. No. 61/286,283, filed Dec. 14, 2009.
Co-pending U.S. Appl. No. 61/297,462, filed Jan. 22, 2010.
Cox J.L., "Cardiac Surgery for Arrhythmias," Journal of Cardiovascular Electrophysiology, 2004, vol. 15, pp. 250-262.
Cox J.L., et al., "Five-Year Experience With the Maze Procedure for Atrial Fibrillation," The Annals of Thoracic Surgery, 1993, vol. 56, pp. 814-824.
Cox J.L., et al., "Modification of the Maze Procedure for Atrial Flutter and Atrial Fibrillation," The Journal of Thoracic and Cardiovascular Surgery, 1995, vol. 110, pp. 473-484.
Cox J.L., "The Status of Surgery for Cardiac Arrhythmias," Circulation, 1985, vol. 71, pp. 413-417.
Cox J.L., "The Surgical Treatment of Atrial Fibrillation," The Journal of Thoracic and Cardiovascular Surgery, 1991, vol. 101, pp. 584-592.
Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet:< URL: http://circ.ahajournals.org/cgi/content/full/91/8/2235>.
Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.
Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.
European Search Report for Application No. EP07799466.3 dated Nov. 18, 2010, 9 pages.
European Search Report for Application No. EP08746822.9 dated Mar. 29, 2010, 7 Pages.
Examination Communication for Application No. EP06734083.6 dated May 18, 2010, 3 Pages.
Extended European Search Report for Application No. EP06734083.6 dated Jul. 1, 2009, 6 pages.
Final Office Action dated Mar. 1, 2010 for U.S. Appl. No. 12/117,655, filed May 8, 2008.
Final Office Action dated Jun. 2, 2011 for U.S. Appl. No. 12/117,655, filed May 8, 2008.
Final Office Action dated May 12, 2011 for U.S. Appl. No. 11/775,771, filed Jul. 10, 2007.
Final Office Action dated Sep. 16, 2010 for U.S. Appl. No. 11/828,267, filed Jul. 25, 2007.
Non-Final Office Action dated Jun. 7, 2011 for U.S. Appl. No. 12/323,281, filed Nov. 25, 2008.
Non-Final Office Action dated Jun. 8, 2009 for U.S. Appl. No. 12/117,655, filed May 8, 2008.
Non-Final Office Action dated May 9, 2011 for U.S. Appl. No. 11/961,950, filed Dec. 20, 2007.
Non-Final Office Action dated May 9, 2011 for U.S. Appl. No. 11/961,995, filed Dec. 20, 2007.
Non-Final Office Action dated May 9, 2011 for U.S. Appl. No. 11/962,029, filed Dec. 20, 2007.
Non-Final Office Action dated Jun. 10, 2010 for U.S. Appl. No. 11/560,742, filed Nov. 16, 2006.
Non-Final Office Action dated Apr. 11, 2011 for U.S. Appl. No. 11/763,399, filed Jun. 14, 2007.
Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.
Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated Jul. 21, 2010 for U.S. Appl. No. 11/687,597, filed Mar. 16, 2007.
Non-Final Office Action dated Apr. 22, 2011 for U.S. Appl. No. 12/367,019, filed Feb. 6, 2009.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,158, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Aug. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Jun. 13, 2011 for Japanese Application No. 2007-554156 filed Jan. 30, 2006.
Notice of Allowance dated Nov. 15, 2010 for U S. U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.

(56) References Cited

OTHER PUBLICATIONS

Notice of Allowance dated Feb. 24, 2011 for U.S. Appl. No. 11/687,597, filed Mar. 16, 2007.
Office Action dated Feb. 15, 2011 for Japanese Application No. 2007-554156 filed Jan. 30, 2006.
Office Action dated Apr. 27, 2011 for Japanese Application No. 2009-500630 filed Mar. 16, 2007.
Supplemental European Search Report for Application No. EP07758716 dated Feb. 28, 2011, 8 Pages.
Supplementary European search report for Application No. EP07812146.4 dated Nov. 18, 2010, 8 Pages.
Supplementary European Search Report for Application No. EP07841754, dated Jun. 30, 2010, 6 pages.
Uchida Y., "Developmental History of Cardioscopes", in: Coronary Angioscopy, Chapter 19, Futura Publishing Company, Inc., 2001, pp. 187-197.

* cited by examiner

METHODS AND APPARATUS FOR PREVENTING TISSUE MIGRATION

CROSS-REFERENCE TO RELATED APPLICATIONS

This application is a continuation of U.S. patent application Ser. No. 11/877,386, filed Oct. 23, 2007, which claims the benefit of priority to U.S. Provisional Patent Application 60/862,575 filed Oct. 23, 20016, which are incorporated herein by reference in their entirety.

FIELD OF THE INVENTION

The present invention relates generally to apparatus and methods used for preventing the migration of a tissue region within a body. More particularly, the present invention relates to apparatus and methods for stabilizing a region of tissue during entry or access therethrough to prevent or inhibit the tissue from migrating or "tenting".

BACKGROUND OF THE INVENTION

During transseptal procedures, the clinician typically advances a catheter into the right atrial chamber of the heart and passes a needle intravascularly from the right atrial chamber of the heart, through the atrial septum, and into the left atrial chamber of the heart.

The clinician should ensure that the instruments are desirably situated proximate to the septal wall prior to advancing the needle because of the associated risks in inadvertently puncturing surrounding anatomy. However, because of the inherent properties of the tissue, difficulties with visualization of the septal wall with respect to a position of the instrument is difficult, particularly under fluoroscopic imaging modalities.

Moreover, when passing an instrument such as a needle through the septum, the septal wall may deform and "tent" around the needle and migrate at least partially into the left atrial chamber. This undesirable tenting may be problematic as the preferred path of the needle may be deflected while also bringing the septum closer to other anatomical structures that could be damaged if the needle were to rapidly puncture through the septum.

Thus, methods and apparatus which are able to provide in vivo information with respect to a position of the tissue wall and piercing instrument are desirable. Moreover, methods and apparatus which additionally provide for a counter-traction force with respect to the tissue wall to be pierced are further desirable for inhibiting or preventing tenting of the tissue around the piercing instrument to enhance safety to the patient.

SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and a piercing instrument translatable through the displaced blood for piercing into the tissue surface within the field of view. Further examples of tissue visualization catheters which may be utilized are shown and described in further detail in U.S. patent application Ser. No. 11/259,498 filed Oct. 25, 2005, which is incorporated herein by reference in its entirety.

Prior to advancing or piercing the tissue wall, e.g., the atrial septal wall, a visual confirmation of the location of the hood relative to the septal wall may be desired to ensure adequate positioning. Thus, quickly ensuring appropriate positioning may be achieved through conventional imaging modalities such as fluoroscopy prior to visualizing through the hood itself. To facilitate the visualization of the hood relative to the septal wall, one or more radiopaque markers may be utilized optionally along the hood itself or along one or more flexible guidewires passed through the hood and into contact against the tissue surface.

With the location of the hood confirmed along the septal wall, the piercing instrument may be deployed for passage into and/or through the underlying tissue. Prior to, during, or even after deployment of the piercing instrument, the visualization hood may be flushed with the transparent fluid and the underlying tissue may be directly visualized. The insertion and/or passage of the piercing instrument may of course be directly visualized during the procedure through the transparent fluid.

The piercing instrument itself may be configured in a number of various configurations for temporarily engaging a region of tissue to be pierced to stabilize the tissue wall so that migration or "tenting" of the tissue around the piercing instrument is inhibited or prevented. Stabilization of the tissue wall may be accomplished during any number of transseptal procedures when intravascularly accessing the various heart chambers.

In one variation, a secondary suctioning hood may be deployed from within the visualization hood and adhered against the tissue surface to be pierced. A vacuum force may be drawn through the suctioning hood to stabilize the tissue with counter-traction while the piercing instrument is passed into and through the tissue. Another variation may utilize a piercing instrument having one or more helical threads which allow the instrument to be screwed into and/or through the tissue. A guidewire or other instrument may then be passed through a lumen defined within the piercing instrument to gain unobstructed access to the body lumen, such as the left atrial chamber.

In yet another variation, tissue grasping members may be deployed from a sheath or tubular member slidably positioned within the visualization hood may be temporarily pinched onto the tissue to provide the counter-traction force during transseptal entry. In yet additional variations, a number of projections or retaining members may be positioned over a circumference of the hood to temporarily engage the underlying tissue to the hood. Thus, instruments may be advanced through the hood and into and/or through the underlying tissue while an engaged periphery of the tissue provides the sufficient counter-traction force.

BRIEF DESCRIPTION OF THE DRAWINGS

FIGS. 14A and 141 show perspective and side views, respectively, of another variation of a hood having one or more radiopaque struts which are fabricated from a radiopaque material or which are inflatable with a radiopaque medium.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulaling the coronary sinus, diagnosis of valve regurgitation/stenosis, valvuloplasty, atrial appendage closure, arrhythmogenic focus ablation, among other procedures. Further examples of tissue visualization catheters which may be utilized are shown and described in further detail in U.S. patent application Ser. No. 11/259,498 filed Oct. 25, 2005, which has been incorporated hereinabove by reference in its entirety.

Figure 1A:
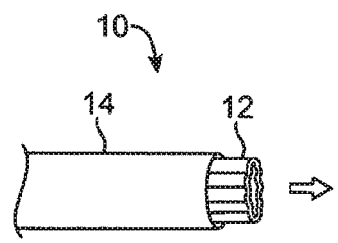
FIG. 1A shows a side view of one variation of a tissue imaging apparatus during deployment from a sheath or delivery catheter.
Figure 1B:
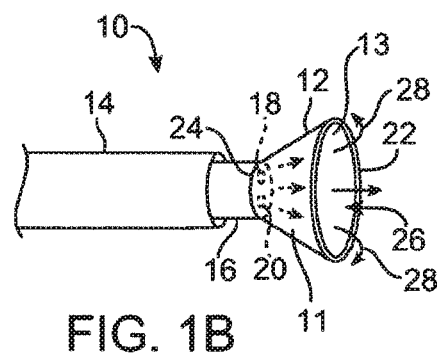
FIG. 1B shows the deployed tissue imaging apparatus of FIG. 1A having an optionally expandable hood or sheath attached to an imaging and/or diagnostic catheter.
Figure 1C:
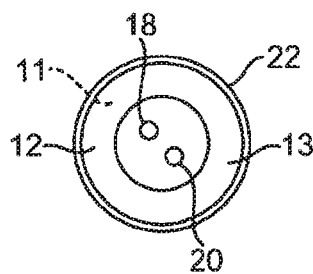
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar (E. I. du Pont de Nemours, Wilmington, Del.), which is an aramid and which can be made into thin. e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
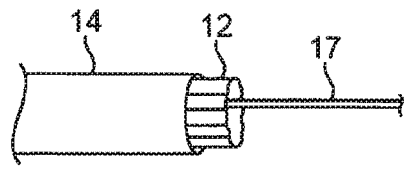
FIGS. 1D to 1F show the apparatus of FIGS. 1A to 1C with an additional lumen, e.g., for passage of a guidewire therethrough.
Figure 1E:
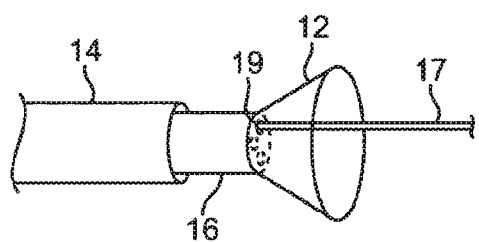
Figure 1F:
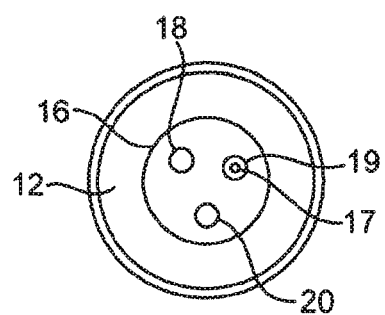

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
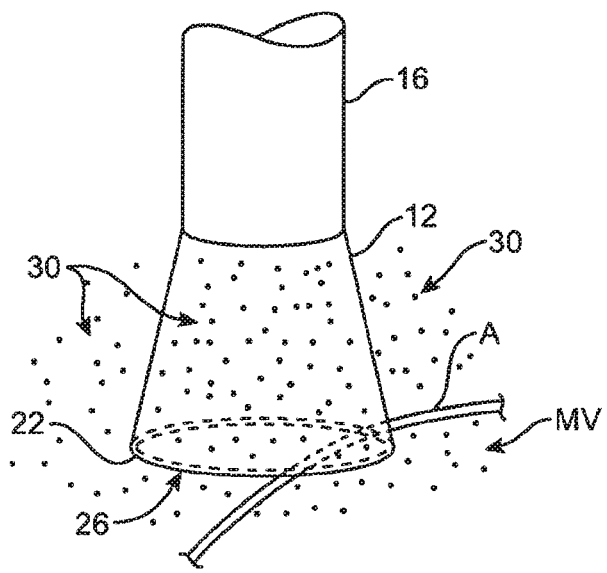
FIGS. 2A and 2B show one example of a deployed tissue imager positioned against or adjacent to the tissue to be imaged and a flow of fluid, such as saline, displacing blood from within the expandable hood.
Figure 2B:
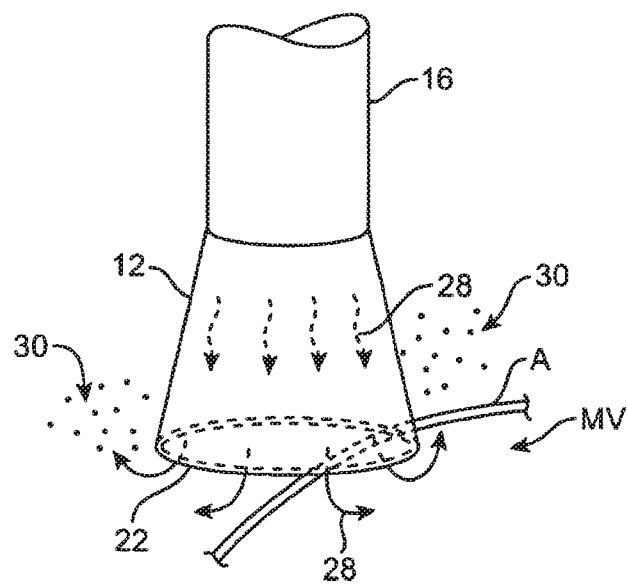

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
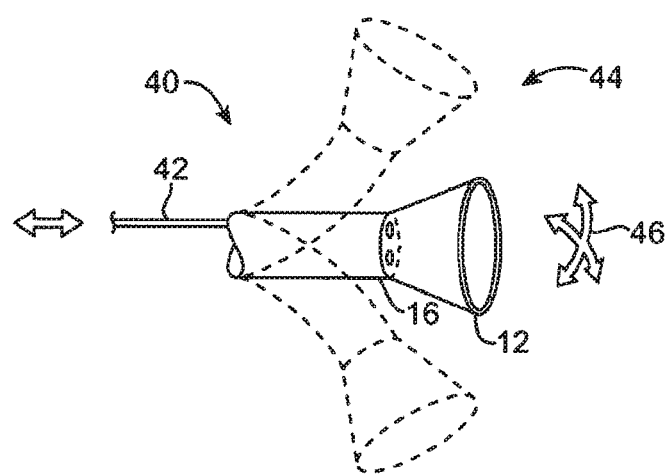
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
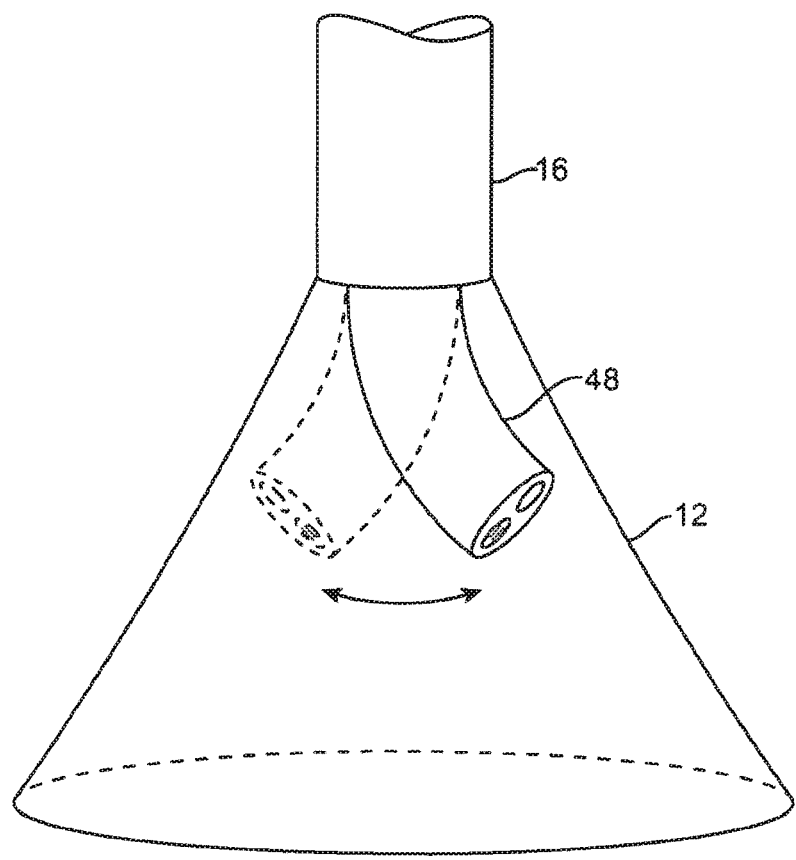
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
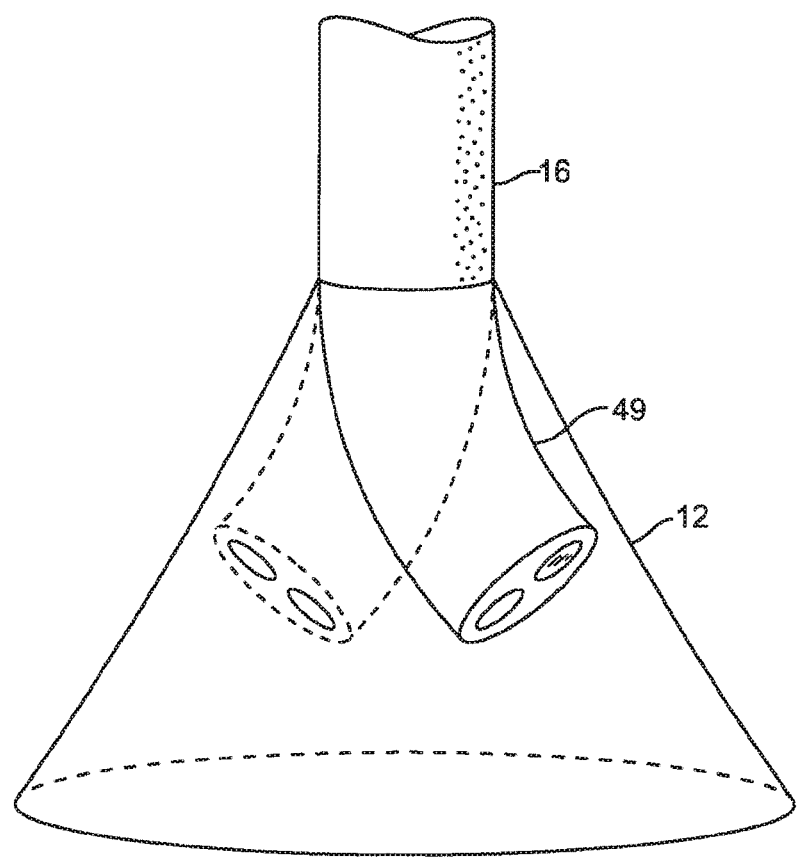

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
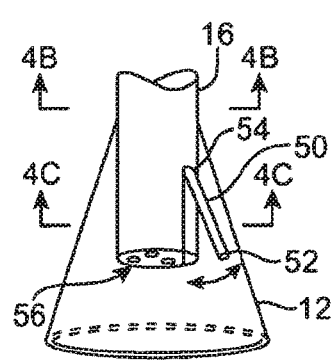
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
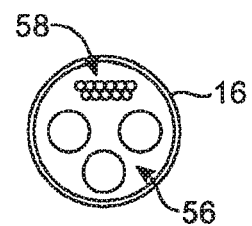
Figure 4C:
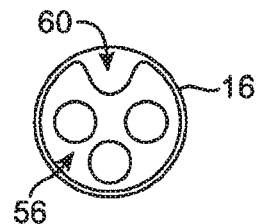

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 4D:
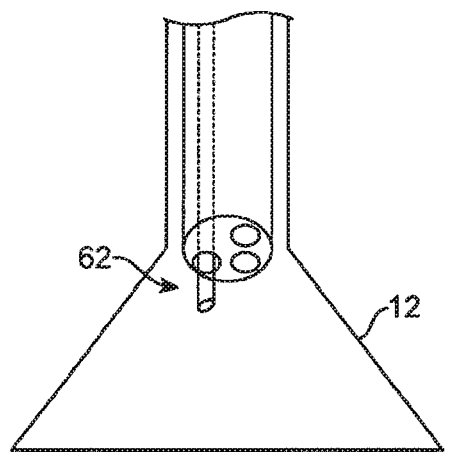
FIGS. 4D and 4E show examples of various visualization imagers which may be utilized within or along the imaging hood.
Figure 4E:
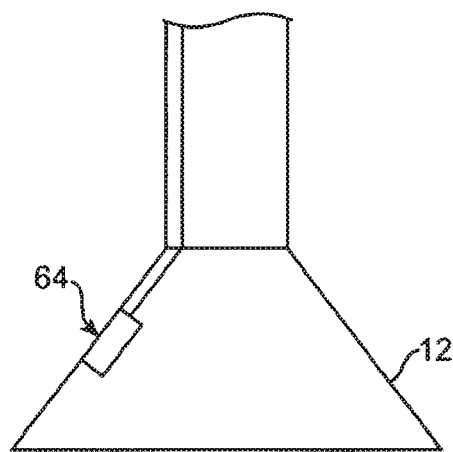

FIG. 4D shows a partial cross-sectional view of an example where one or more optical fiber bundles 62 may be positioned within the catheter and within imaging hood 12 to provide direct in-line imaging of the open area within hood 12. FIG. 4E shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 5:
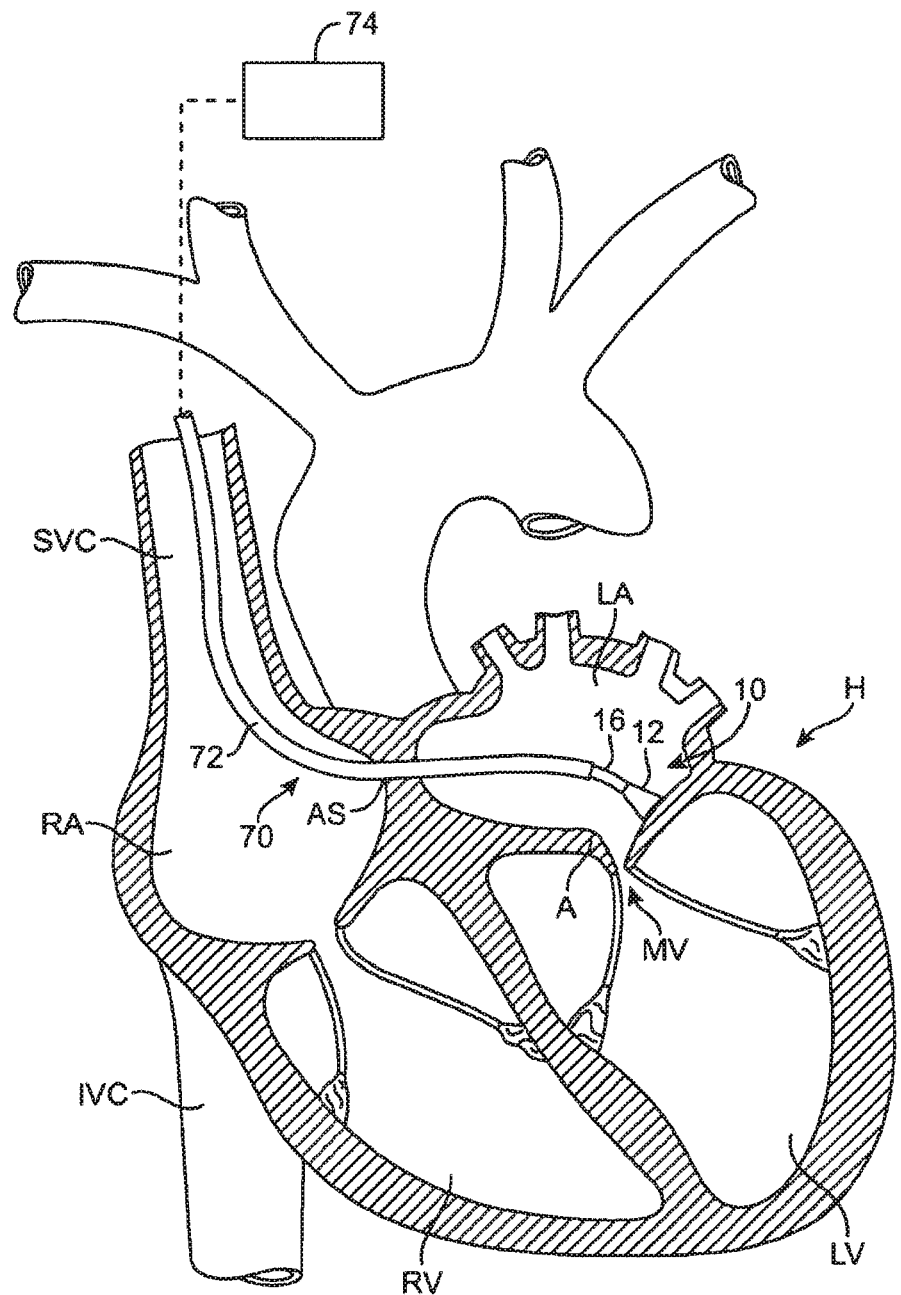
FIG. 5 shows an illustrative view of an example of a tissue imager advanced intravascularly within a heart for imaging tissue regions within an atrial chamber.

FIG. 5 shows an illustrative cross-sectional view of a heart H having tissue regions of interest being viewed via an imaging assembly 10. In this example, delivery catheter assembly 70 may be introduced percutaneously into the patient's vasculature and advanced through the superior vena cava SVC and into the right atrium RA. The delivery catheter or sheath 72 may be articulated through the atrial septum AS and into the left atrium LA for viewing or treating the tissue, e.g., the annulus A, surrounding the mitral valve MV. As shown, deployment catheter 16 and imaging hood 12 may be advanced out of delivery catheter 72 and brought into contact or in proximity to the tissue region of interest. In other examples, delivery catheter assembly 70 may be advanced through the inferior vena cava IVC, if so desired. Moreover, other regions of the heart H. e.g., the right ventricle RV or left ventricle LV, may also be accessed and imaged or treated by imaging assembly 10.

In accessing regions of the heart H or other parts of the body, the delivery catheter or sheath 14 may comprise a conventional intra-vascular catheter or an endoluminal delivery device. Alternatively, robotically-controlled delivery catheters may also be optionally utilized with the imaging assembly described herein, in which case a computer-controller 74 may be used to control the articulation and positioning of the delivery catheter 14. An example of a robotically-controlled delivery catheter which may be utilized is described in further detail in US Pat. Pub. 2002/0087169 A1 to Brock et al. entitled "Flexible Instrument", which is incorporated herein by reference in its entirety. Other robotically-controlled delivery catheters manufactured by Hansen Medical, Inc. (Mountain View, Calif.) may also be utilized with the delivery catheter 14.

Figure 6A:
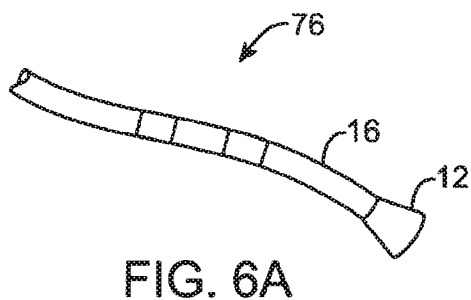
FIGS. 6A to 6C illustrate deployment catheters having one or more optional inflatable balloons or anchors for stabilizing the device during a procedure.
Figure 6B:
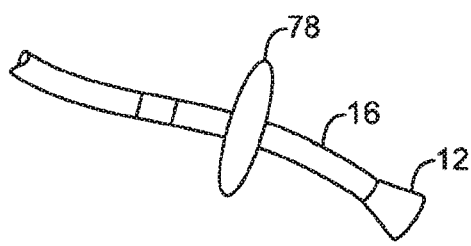
Figure 6C:
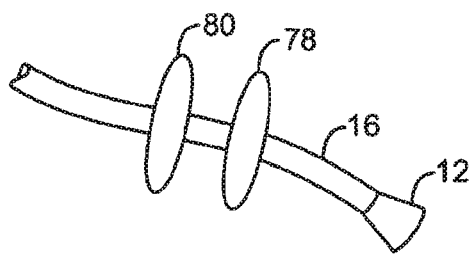

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
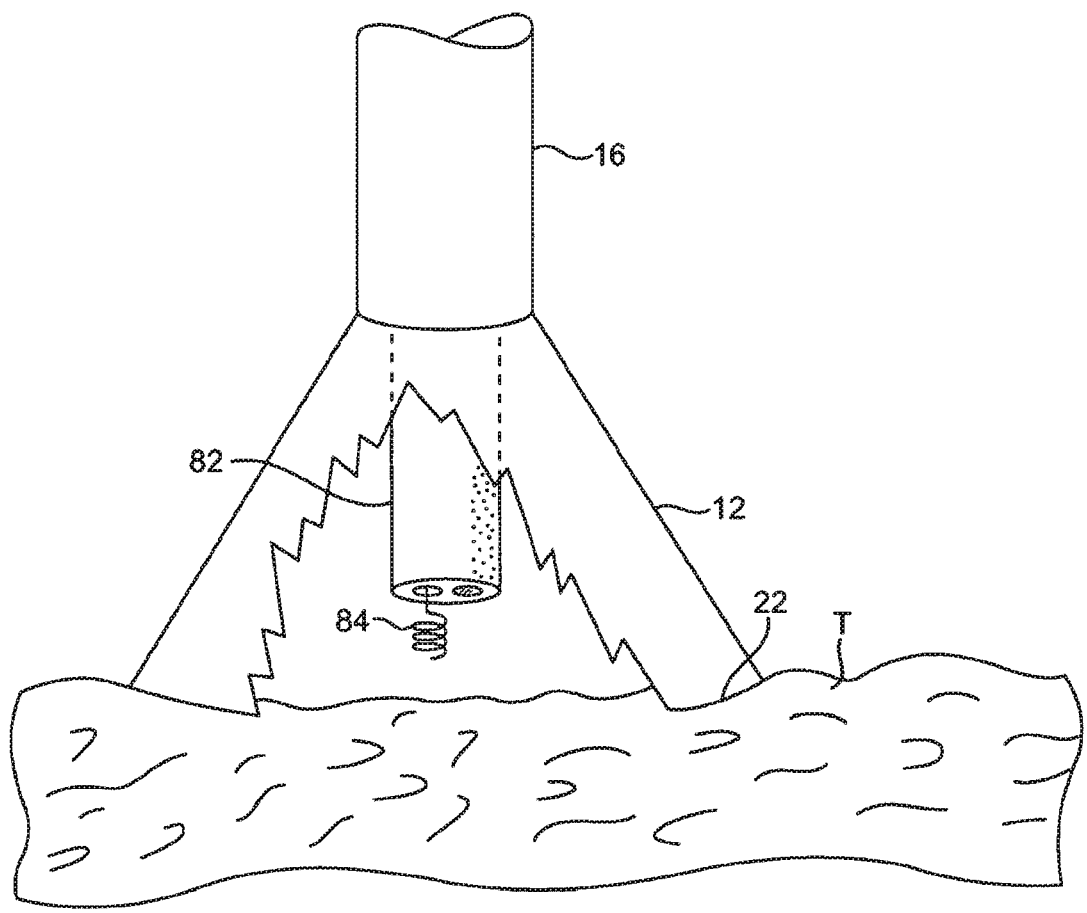
FIGS. 7A and 7B illustrate a variation of an anchoring mechanism such as a helical tissue piercing device fir temporarily stabilizing the imaging hood relative to a tissue surface.
Figure 7B:
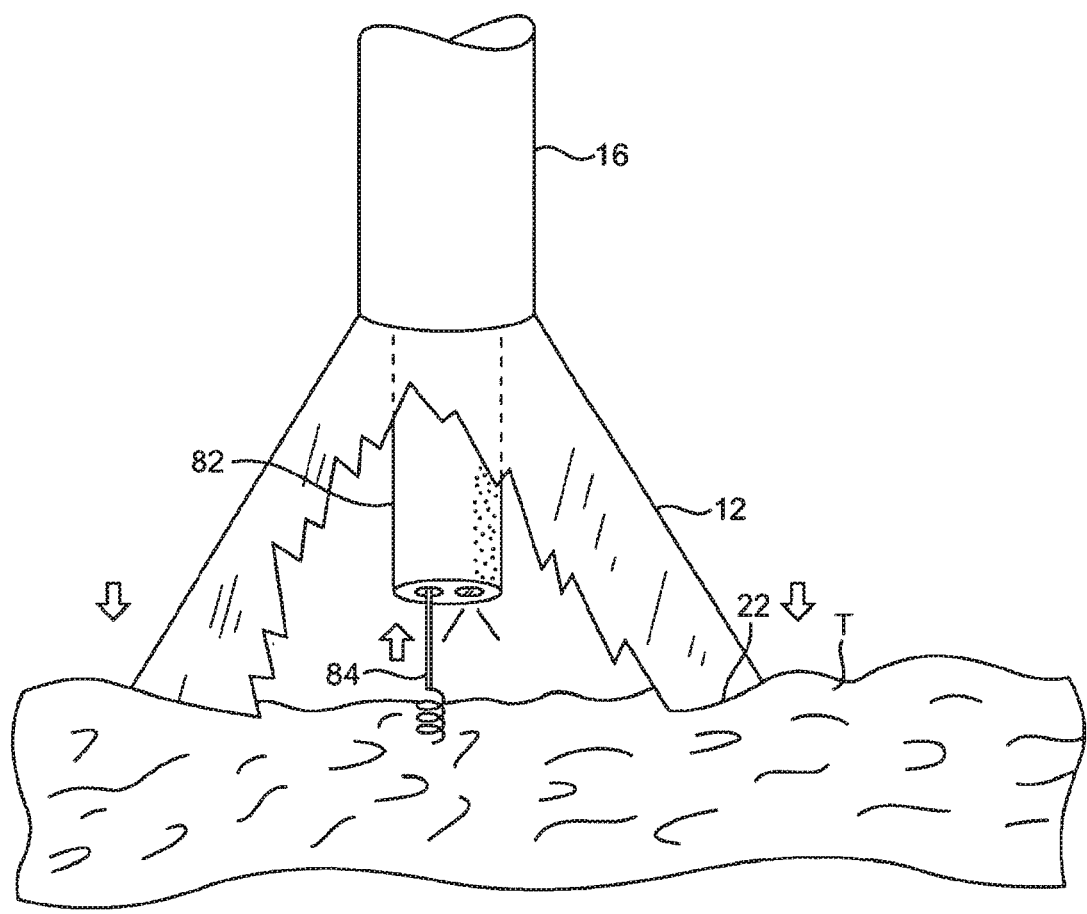

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, anchoring mechanisms such as a helical tissue piercing device 84 may be passed through the tool delivery catheter 82, as shown in FIG. 7A, and into imaging hood 12.

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7I, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. Alter a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
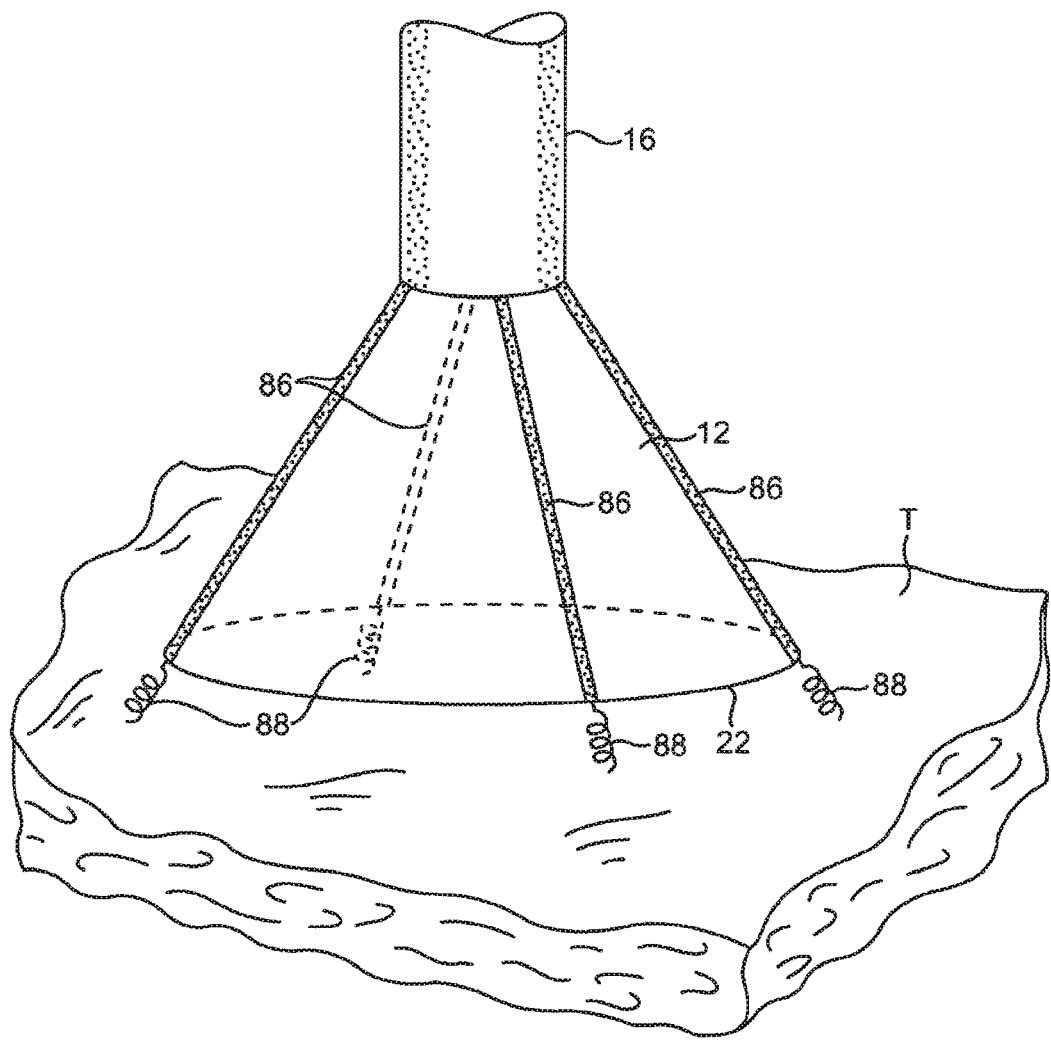
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
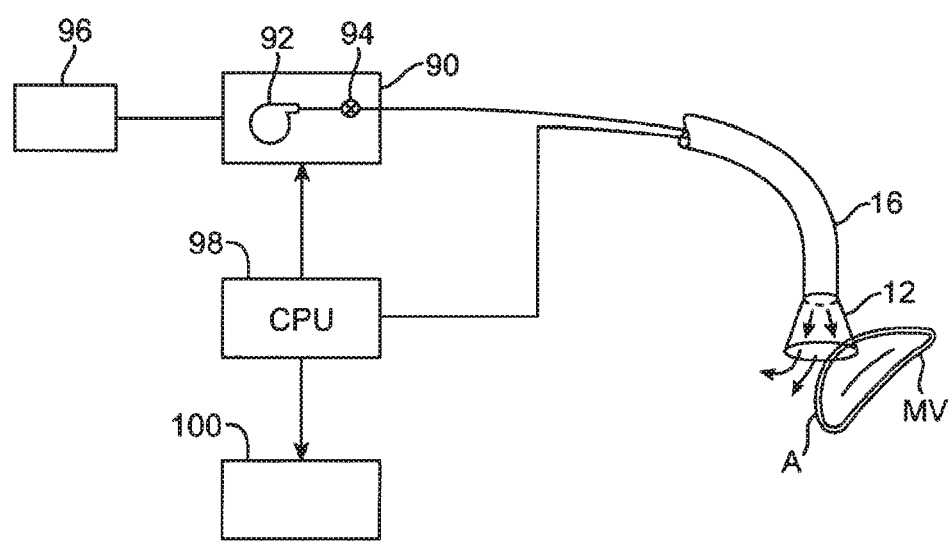
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
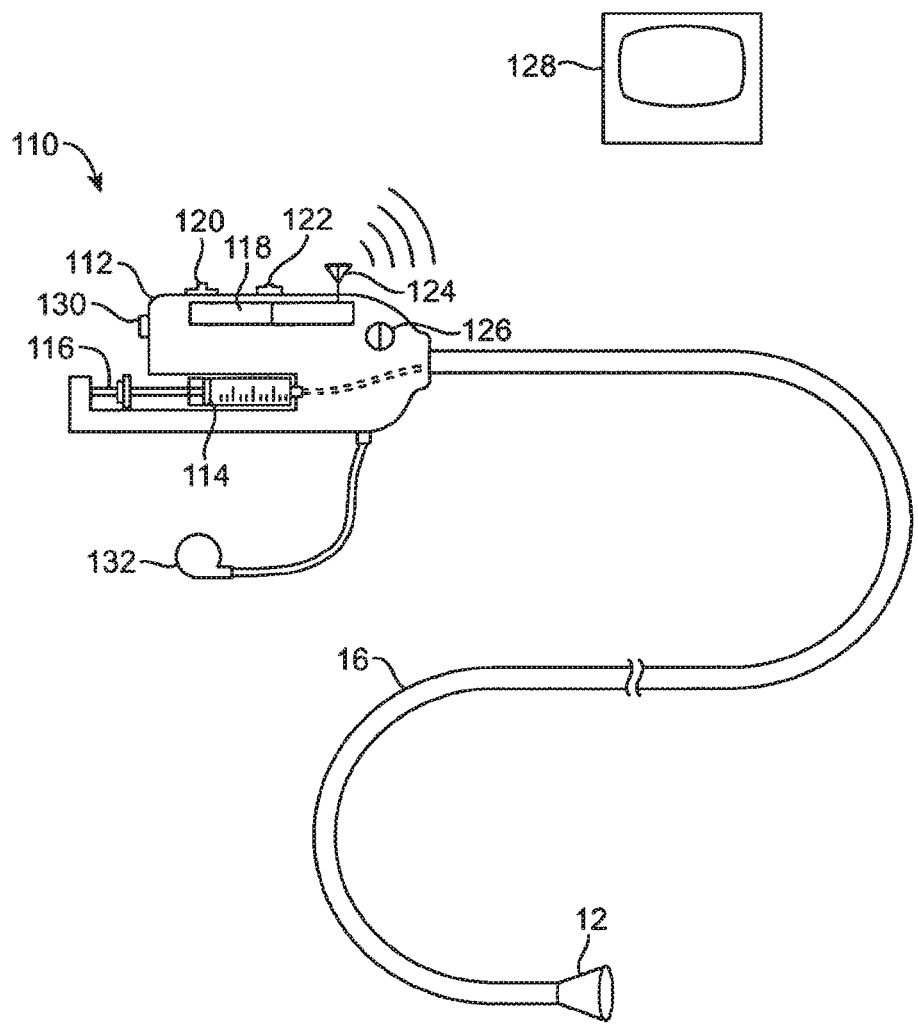
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
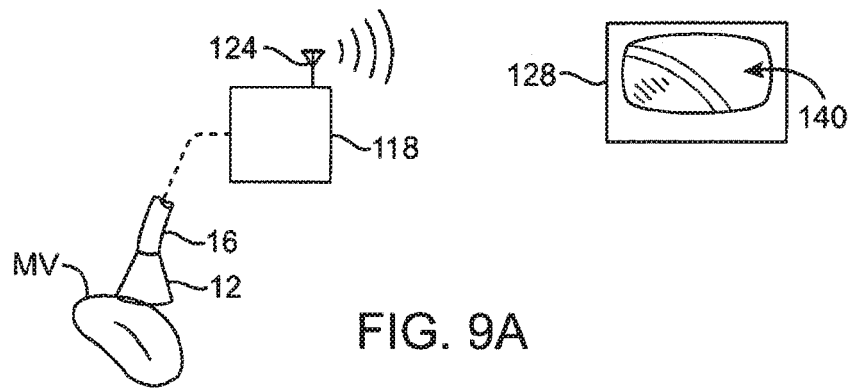
FIGS. 9A to 9C illustrate an example of capturing several images of the tissue at multiple regions.
Figure 9B:
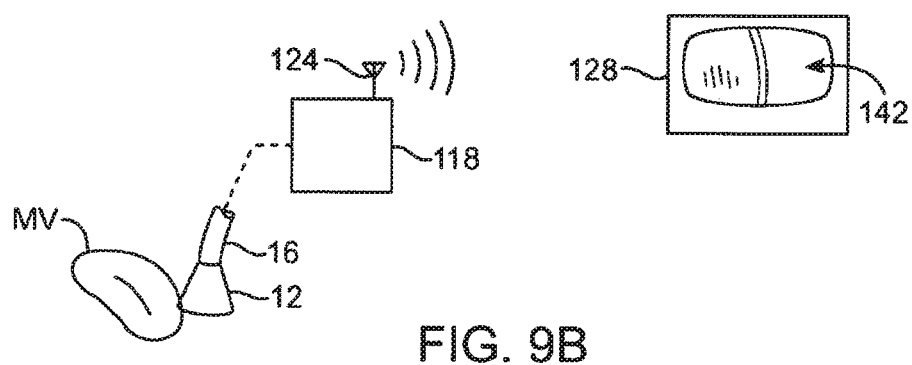
Figure 9C:
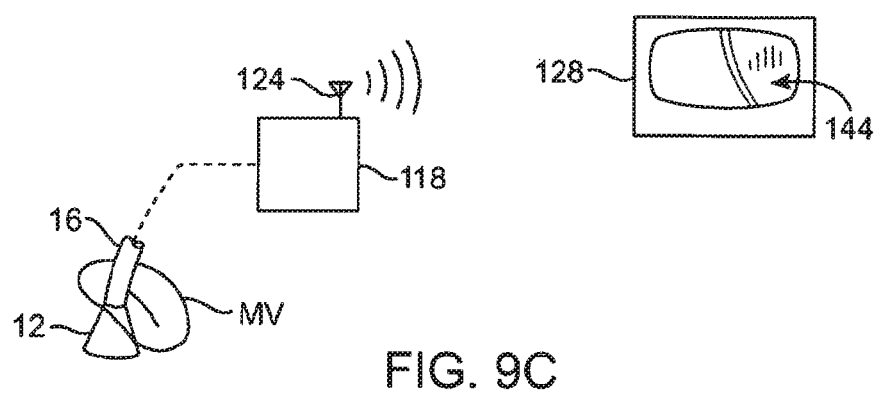

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 144) may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10A:
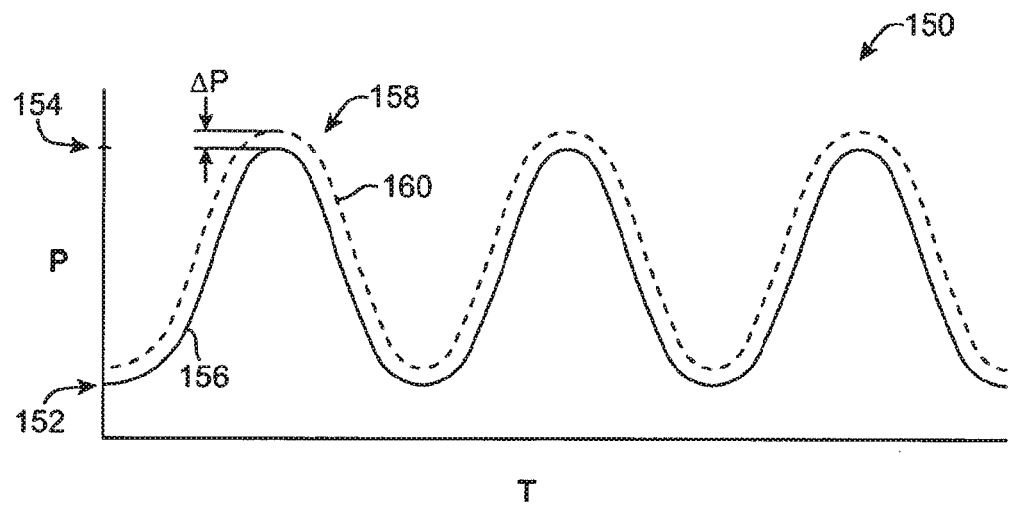
FIGS. 10A and 10B show charts illustrating how fluid pressure within the imaging hood may be coordinated with the surrounding blood pressure; the fluid pressure in the imaging hood may be coordinated with the blood pressure or it may be regulated based upon pressure feedback from the blood.

One example is shown in FIG. 10A which shows a chart 150 illustrating how fluid pressure within the imaging hood 12 may be coordinated with the surrounding blood pressure. Chart 150 shows the cyclical blood pressure 156 alternating between diastolic pressure 152 and systolic pressure 154 over time T due to the beating motion of the patient heart. The fluid pressure of the imaging fluid, indicated by plot 160, within imaging hood 12 may be automatically timed to correspond to the blood pressure changes 160 such that an increased pressure is maintained within imaging hood 12 which is consistently above the blood pressure 156 by a slight increase ΔP, as illustrated by the pressure difference at the peak systolic pressure 158. This pressure difference, ΔP, may be maintained within imaging hood 12 over the pressure variance of the surrounding blood pressure to maintain a positive imaging fluid pressure within imaging hood 12 to maintain a clear view of the underlying tissue. One benefit of maintaining a constant ΔP is a constant flow and maintenance of a clear field.

Figure 10B:
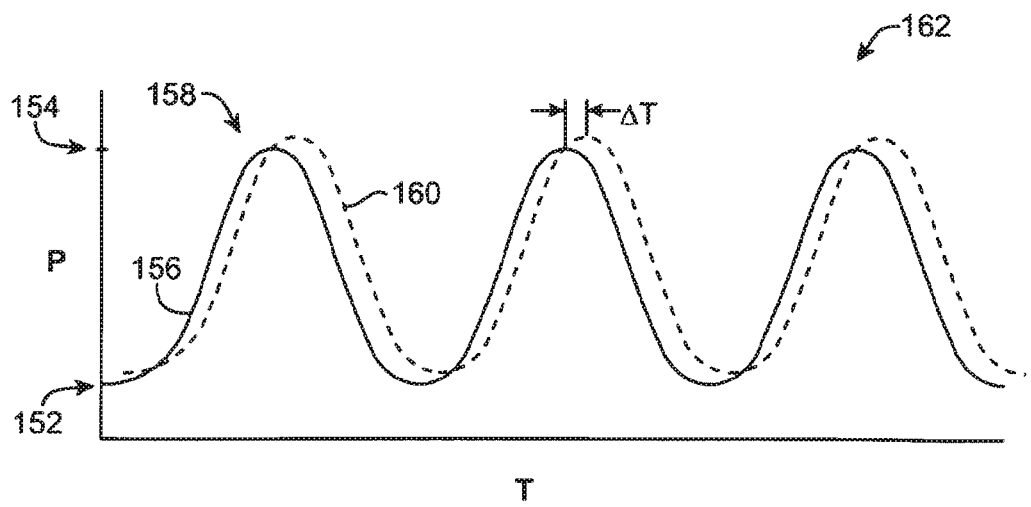

FIG. 10B shows a chart 162 illustrating another variation for maintaining a clear view of the underlying tissue where one or more sensors within the imaging hood 12, as described in further detail below, may be configured to sense pressure changes within the imaging hood 12 and to correspondingly increase the imaging fluid pressure within imaging hood 12. This may result in a time delay, ΔT, as illustrated by the shifted fluid pressure 160 relative to the cycling blood pressure 156, although the time delays ΔT may be negligible in maintaining the clear image of the underlying tissue. Predictive software algorithms can also be used to substantially eliminate this time delay by predicting when the next pressure wave peak will arrive and by increasing the pressure ahead of the pressure wave's arrival by an amount of time equal to the aforementioned time delay to essentially cancel the time delay out.

The variations in fluid pressure within imaging hood 12 may be accomplished in part due to the nature of imaging hood 12. An inflatable balloon, which is conventionally utilized for imaging tissue, may be affected by the surrounding blood pressure changes. On the other hand, an imaging hood 12 retains a constant volume therewithin and is structurally unaffected by the surrounding blood pressure changes, thus allowing for pressure increases therewithin. The material that hood 12 is made from may also contribute to the manner in which the pressure is modulated within this hood 12. A stiffer hood material, such as high durometer polyurethane or Nylon, may facilitate the maintaining of an open hood when deployed. On the other hand, a relatively lower durometer or softer material, such as a low durometer PVC or polyurethane, may collapse from the surrounding fluid pressure and may not adequately maintain a deployed or expanded hood.

In utilizing the devices and systems, a tissue wall such as the atrial septal wall may be pierced while under direct visualization through the imaging hood, e.g., crossing an atrial septal wall from a right atrial chamber to a left atrial chamber within a patient's heart. However, prior to advancing or piercing the septal wall, visual confirmation of the location of the hood relative to the septal wall may be desired to ensure adequate positioning. Thus, quickly ensuring appropriate positioning may be achieved through, e.g., conventional imaging modalities such as fluoroscopy, prior to or during visualizing through the hood itself. Other common input sources may include tactile feedback from the instrument, fluoroscopic imaging, and ultrasonic visualization, etc. Typically, ultrasonic visualization is captured through a separate catheter placed in or near the patient's heart while fluoroscopic visualization relies on the differences in radiopacity of various devices or injections of radiopaque contrast media. The septum and fossa are typically not sufficiently radiopaque to be readily fluoroscopically visible.

One method of increasing the radiopacity of the instruments is to fabricate them completely from or at least partially from a material that itself is radiopaque. Another method would be to the instruments with a radiopaque material. Examples of radiopaque materials may include, but not limited to, barium, barium sulfate, gold, platinum, tungsten, iridium, rhenium, etc., or any combination of these materials.

Figure 11A:
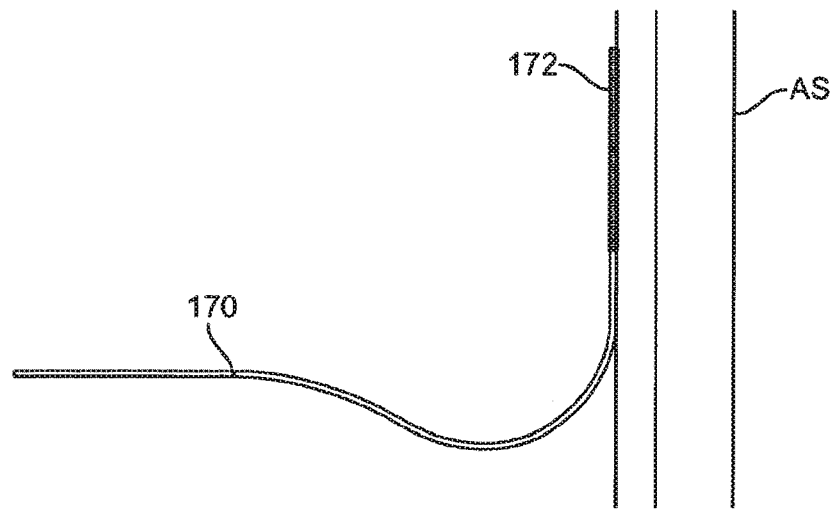
FIGS. 11A and 11B show side views of one variation for confirming hood positioning against the tissue wall using a flexible guide member or guidewire having a radiopaque distal end and the member placed against the tissue wall underlying the visualization hood, respectively.
Figure 11B:
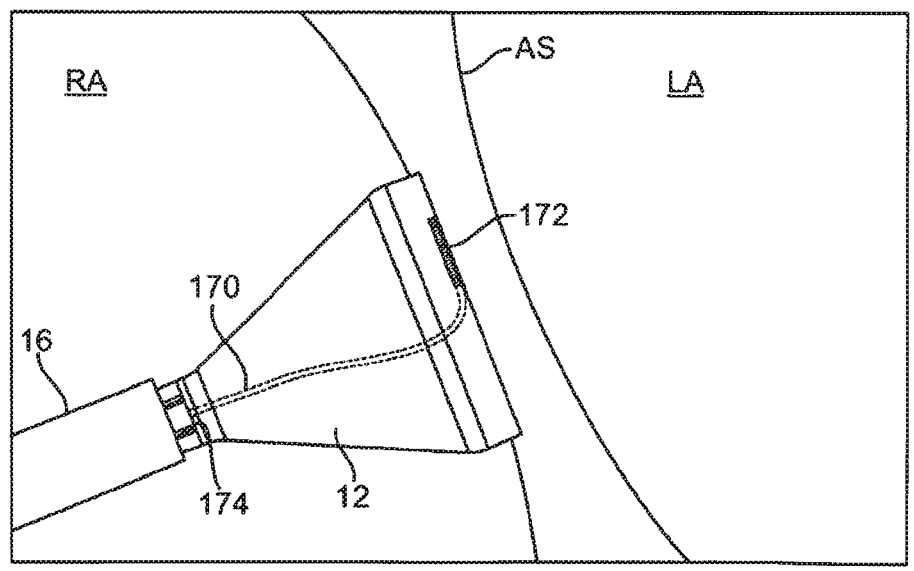

Another solution to providing additional fluoroscopic imaging guidance may include use a flexible component placed against the septum wall. Such an element would be radiopaque to allow the clinician to approximate or locate the septum wall by the appearance and position of the flexible component. One example of a flexible member is shown in the side views of FIGS. 11A and 11B which illustrate a flexible guide member or guidewire 170 having a radiopaque distal end 172 advanced through or along a lumen 174 of the deployment catheter 16 for confirming hood positioning against the surface of the atrial septum AS underlying the visualization hood 12. In use, once the barrier, membrane, or hood 12 has been advanced proximate to or against a septal tissue surface AS, the radiopaque distal end 172 of the guidewire 170 may be advanced into and through the hood 12 until the radiopaque distal end 172 contacts and slides against the septal wall AS, as shown in FIG. 1B. Under fluoroscopic imaging, the position of the radiopaque guidewire end 172 may be visualized and the location of the septal wall AS may be determined when the guidewire end 172 is contacted against the tissue surface. Moreover, the placement of the guidewire 170 may be under direct visual guidance or in conjunction with the visualization catheter, which operates in part by flushing the hood with a clear fluid and directly visualizing the underlying tissue through the fluid, as described above.

Figure 12A:
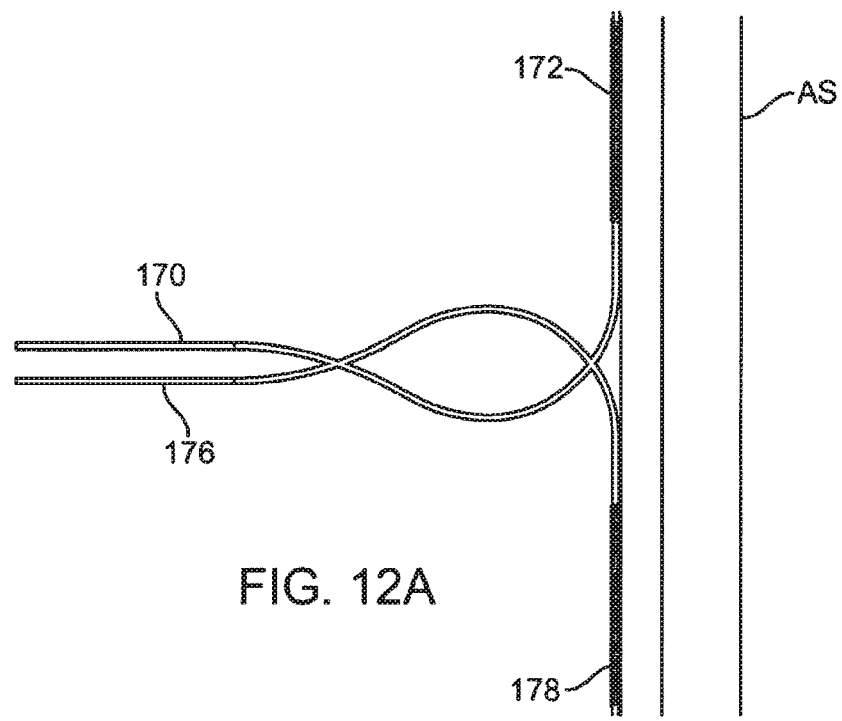
FIGS. 12A and 12B show side views of another variation for confirming hood positioning against the tissue wall using two flexible guide members or guidewires each having a radiopaque distal end and the members placed against the tissue wall underlying the visualization hood, respectively.
Figure 12B:
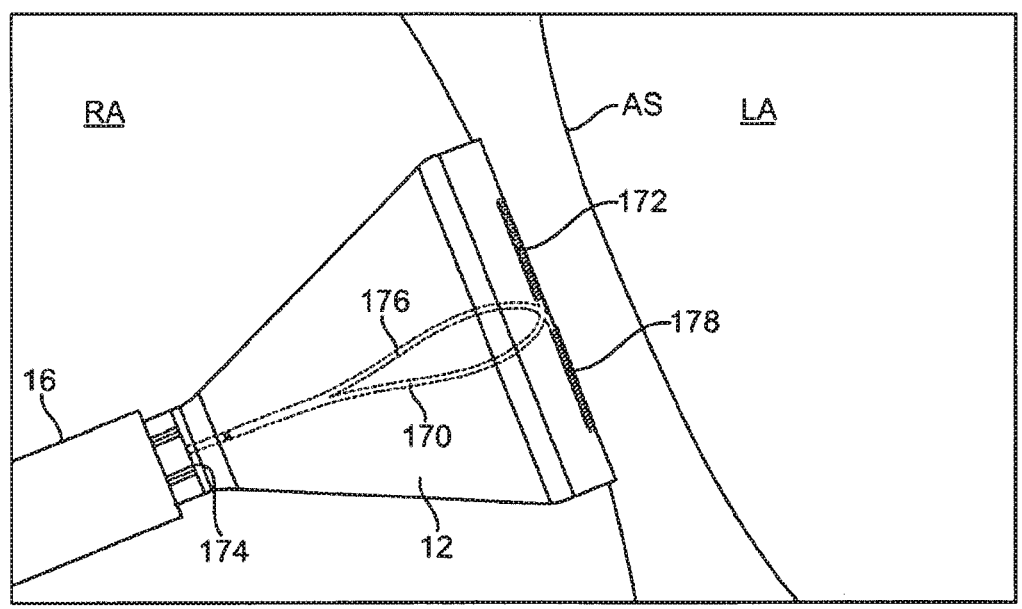

In another variation, multiple flexible guide members or guidewires 170, 176 each having a radiopaque distal end portion 172, 178, respectively, may be utilized, as shown in the side views of FIGS. 12A and 12B. The position of the septum wall can be approximated or determined under fluoroscopic imaging when the distal end of the plurality of guidewires 170, 176 are found to slide along the septum wall AS. Although two guidewires 170, 176 are illustrated, three or more members may be utilized, as practicable, and each member may also be configured to bend or slide along the tissue surface in opposing directions such that a profile or contour of the tissue surface may be ascertained when visualized.

Figure 13A:
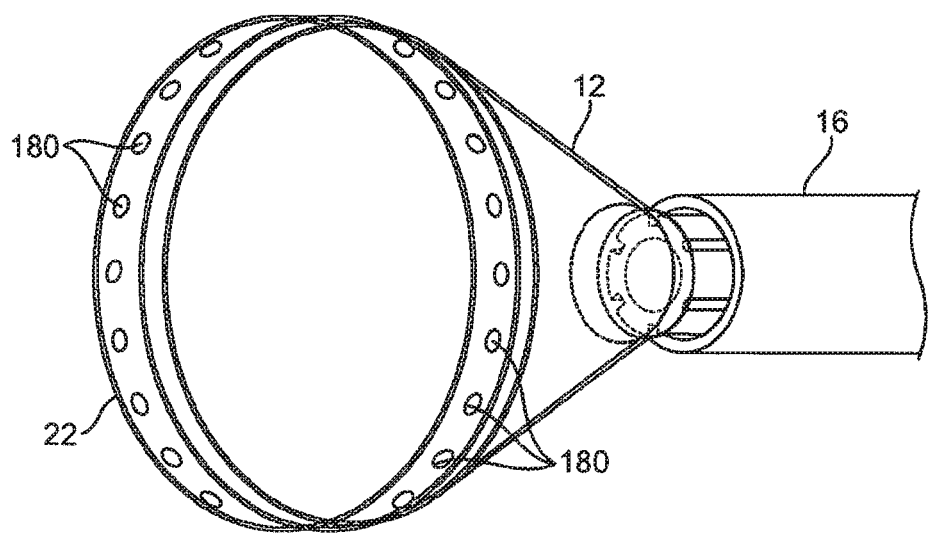
FIGS. 13A and 13B show perspective and side views, respectively, of a hood having a plurality of radiopaque elements, e.g., beads, positioned around the circumference of the hood.
Figure 13B:
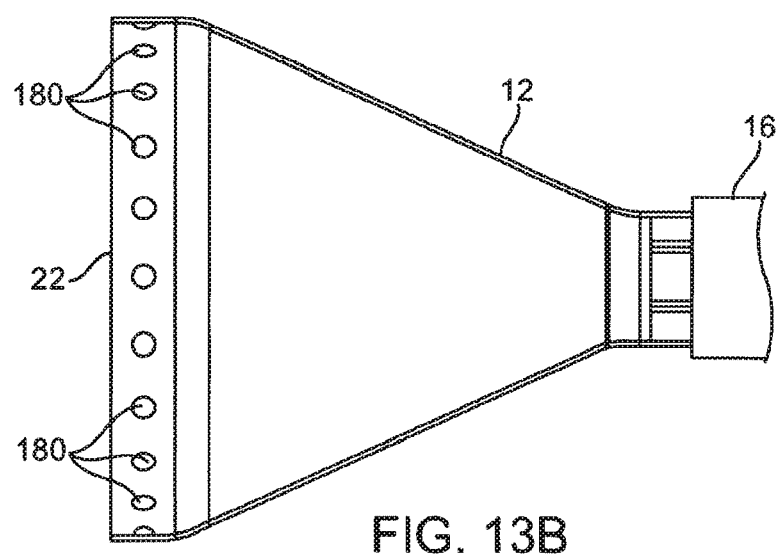

FIGS. 13A and 13B show perspective and side views, respectively, of a hood having a plurality of radiopaque elements 180, e.g., beads, positioned around the circumference of the hood 12. e.g., upon or proximal to a circumference of contact lip or edge 22, for ascertaining a location of the hood relative to the tissue surface. The radiopaque elements 180 may be uniformly spaced around hood 12 or they may be spaced apart relative to one another depending upon the desired pattern.

Figure 14A:
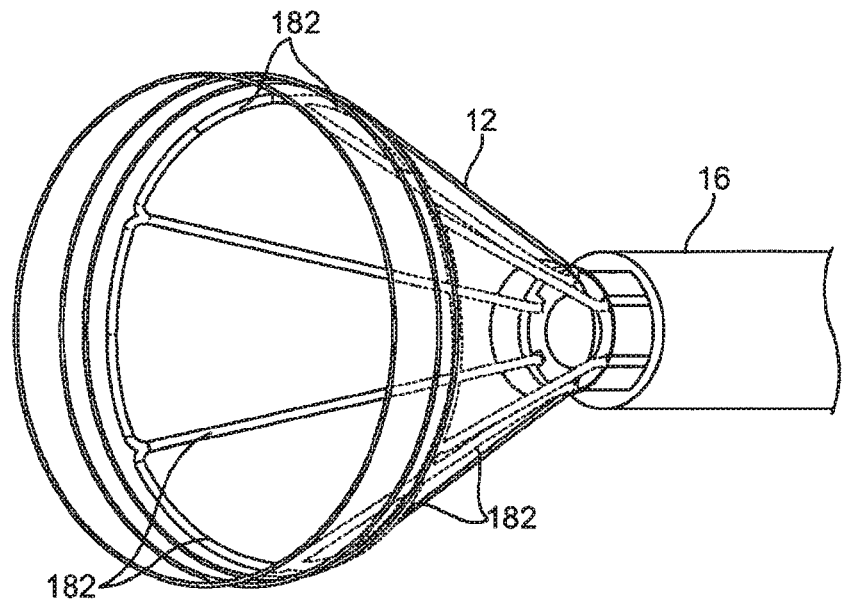
Figure 14B:
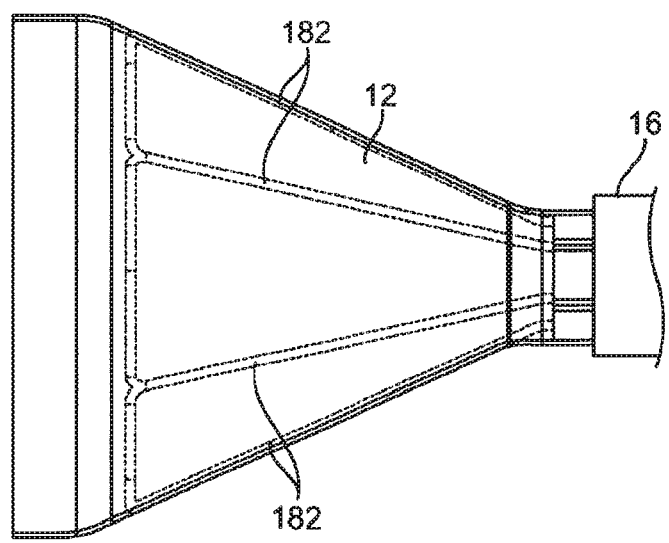

FIGS. 14A and 14B show perspective and side views, respectively, of another variation of a hood having one or more radiopaque struts 182 which may be fabricated from a radiopaque material (described above) or which are inflatable with a radiopaque contrast medium. The struts 182 may be integrated or embedded directly into hood 12 or attached separately. Moreover, the struts 182 may be integrated along longitudinal portions of hood 12 they may be configured as a scaffolding, as shown. Aside from providing radiopacity to hood 12, struts 182 may also provide structural support to the hood 12 when inflated or expanded as a strut or other element.

Figure 15A:
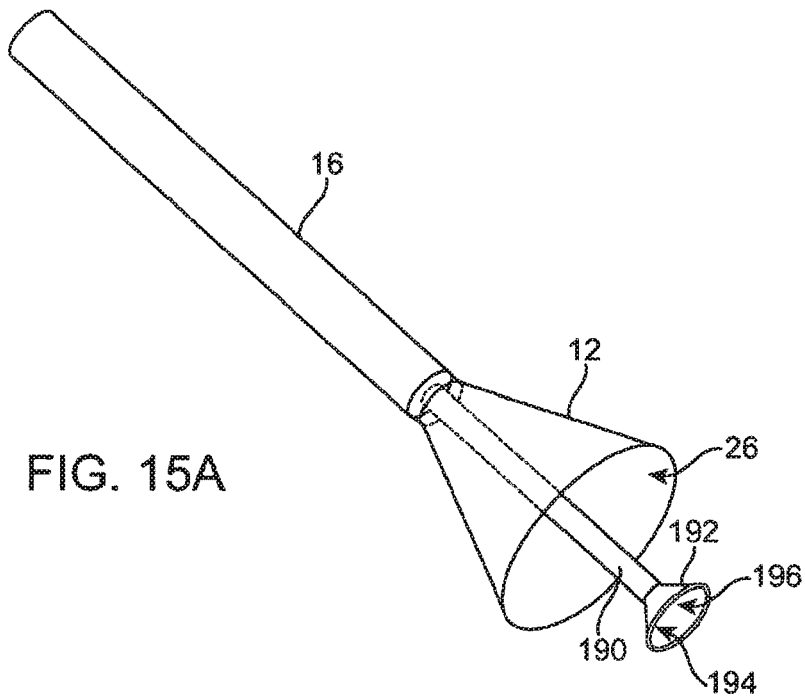
FIGS. 15A and 15B show perspective and side views, respectively, of another variation of the tissue visualization catheter having a double hood configuration in which a radiopaque contrast medium may be injected in the volume between the two hoods for determining hood position along the tissue wall.
Figure 15B:
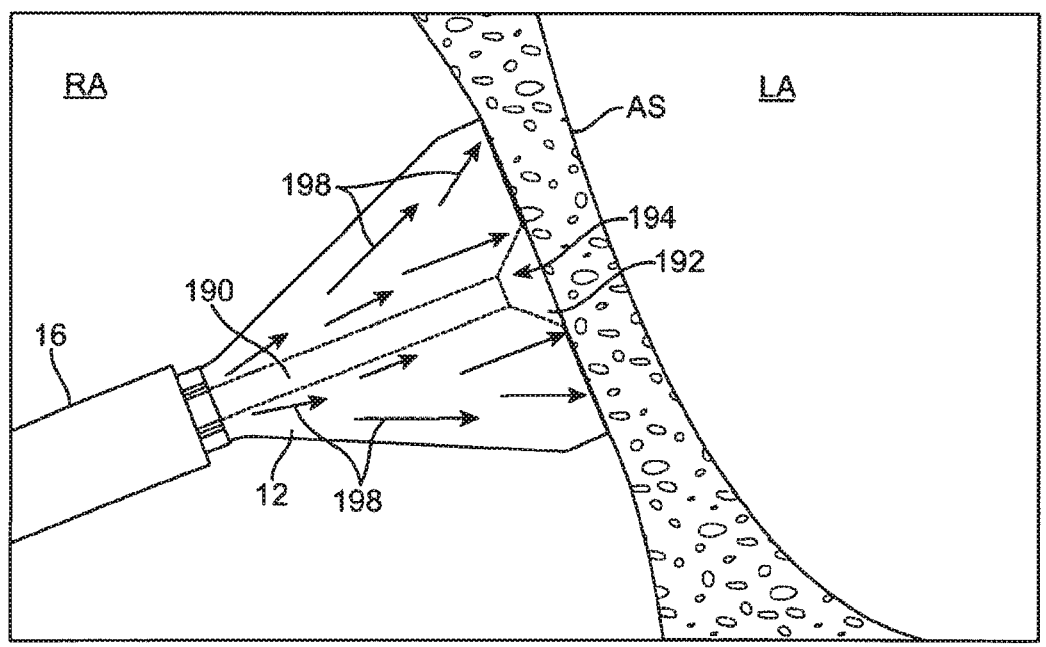

Yet another variation is shown in the perspective view of FIG. 15A, which illustrates a tubular member 190 having a secondary hood 192 which defines a secondary open area 194 slidably disposed within hood 12. Secondary hood 192 may be of a size which is relatively smaller than hood 12 such that secondary hood 192 may be easily translated through hood 12. Secondary inner hood 192 may be placed or engaged, such as via a vacuum force, against the underlying tissue surface and the surrounding outer hood 12 may also be placed or secured against the tissue surface. The volume of open area 26 defined between the secondary hood 192 and outer hood 12 may be filled with radiopaque contrast medium 198, as shown in FIG. 15B, to provide a visual determination of a position of hood 12 with respect to the septal tissue surface AS.

Secondary hood 192 can also be used to pass tools, such as needles, guidewires, etc., through a lumen 196 defined through tubular member 190 and also provide visualization via a CCD camera or fiberscope within secondary hood 192 while a transseptal procedure is being performed. The suction hood 192 may also provide stability and better sealing between the tissue surface AS and hood 12, particularly when instruments are advanced into and/or through the underlying atrial septum AS. Further examples of such a secondary suction hood and its uses are described in detail in U.S. patent application Ser. No. 11/775,771 filed Jul. 10, 2007, which is incorporated herein by reference in its entirety.

With the location of hood 12 confirmed along the septal wall, a piercing instrument may be deployed for passage into and/or through the underlying tissue. Prior to, during, or even after deployment of the piercing instrument, the visualization hood 12 may be flushed with the transparent fluid and the septal wall may be directly visualized. The insertion and/or passage of the piercing instrument may of course be directly visualized during the procedure through the transparent fluid.

Figure 16A:
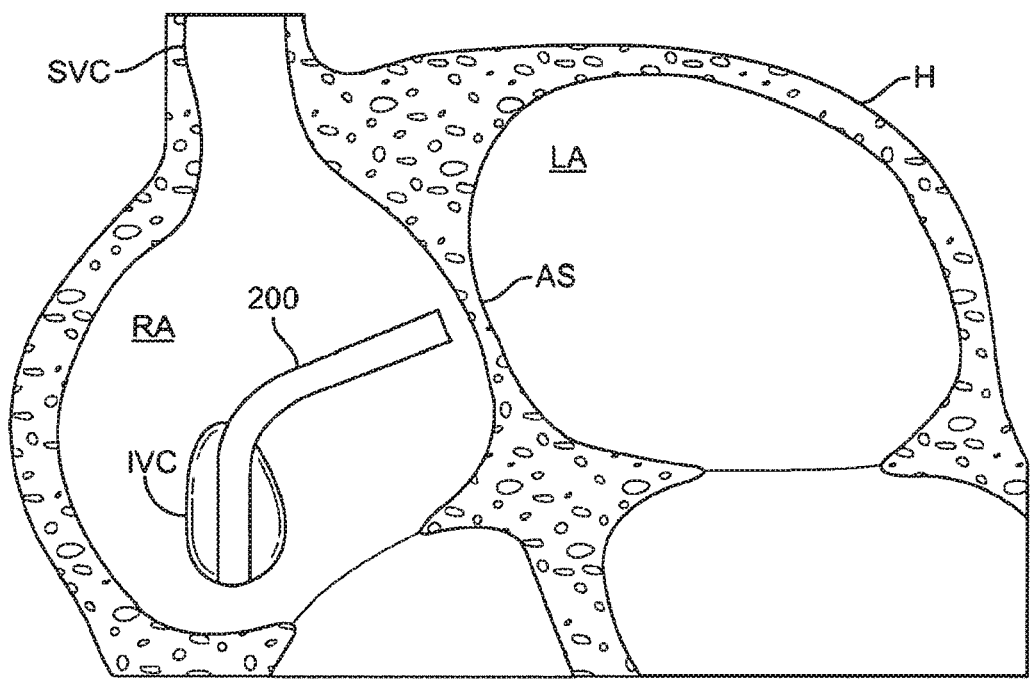
FIG. 16A shows a partial cross-sectional view of the heart with a tissue visualization catheter intravascularly advanced within a right atrial chamber of a patient heart and approaching the atrial septal wall.
Figure 16B:
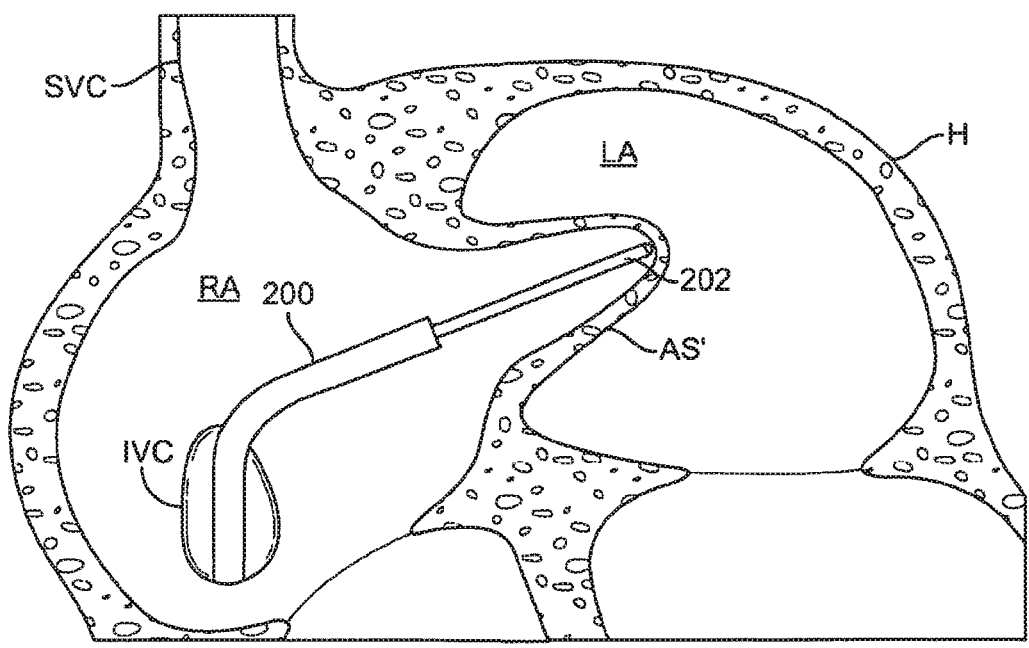
FIG. 16B shows an example of tissue migration or "tenting" of the septal wall around a needle or other instrument attempting to pass into or through the tissue wall.

With catheter 200 advanced intravascularly into the right atrial chamber RA, such as through the inferior vena cava IVC, and positioned proximate or adjacent the atrial septum AS, as shown in FIG. 16A, the piercing instrument 202 (such as a needle) may be deployed to pass into and/or through the atrial septum AS. However, the septal wall AS' may deform and "tent" around the instrument 202 and migrate at least partially into the left atrial chamber LA, as shown in FIG. 16B. This undesirable tenting may be problematic as the preferred path of the instrument 202 may be deflected while also bringing the deformed septum AS' closer to other anatomical structures that could be damaged if the instrument 202 were to rapidly puncture through the septum AS'.

Figure 17:
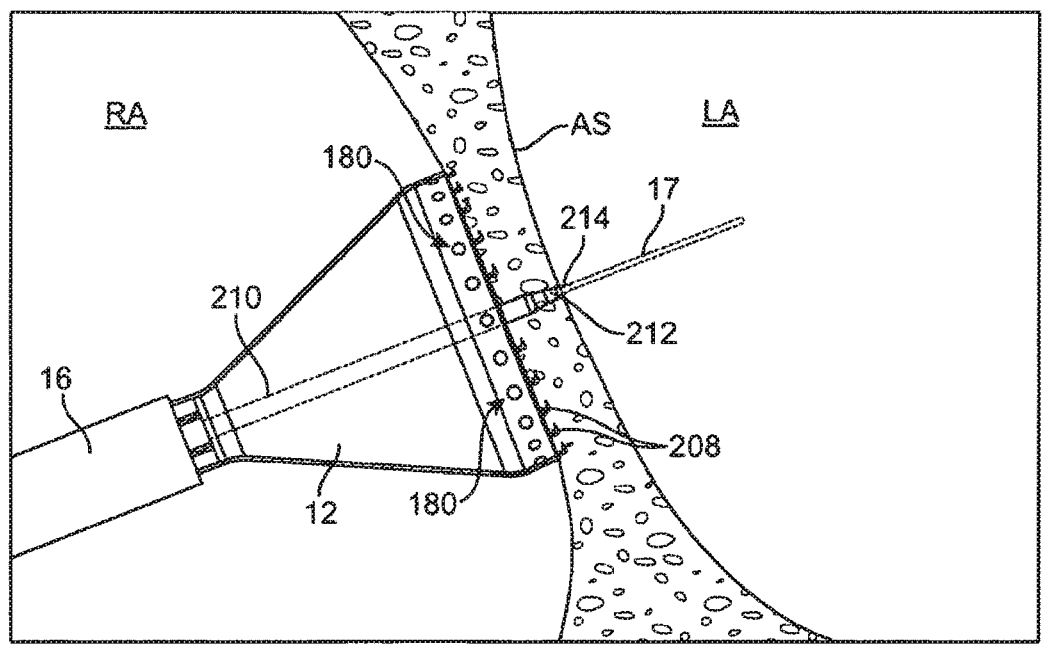
FIG. 17 shows a cross sectional view of the heart illustrating a radiopaque hood having a plurality of optional engagement teeth temporarily affixed to the tissue and further deploying a threaded engaging needle rotated at least partially through the tissue wall to perform a transseptal procedure without any "tenting" effects.

One approach for providing counter-traction against the tissue to inhibit or prevent such tenting is to use a threaded needle instrument 210 having an elongate support member with a threaded distal end 212 that may be advanced into and/or through the septum AS via a controlled rotational or torquing advancement, as shown in FIG. 17. This threaded instrument 210 may be passed through the visualization catheter hood 12 and engaged or threaded through the underlying septal tissue wall AS. Such a threaded element may include any number of threaded instruments, such as a corkscrew or cylindrical screw, etc. The threaded instrument 210 may include a lumen 214 through the instrument to allow passage of other tools therethrough, e.g., such as needles or guidewires 17, etc.

As further shown in FIG. 17, the tissue visualization catheter may optionally include radiopaque hood 12 having any of the one or more radiopaque elements, such as elements 180 around a circumference of hood 12 to aid in visualizing the hood location relative to the septal wall. Moreover, hood 12 may be temporarily affixed to the septal wall AS via one or more optional engaging elements 208 projecting from hood 12 (as described in further detail below) while threaded instrument 210 is rotated into or through the septum AS without tenting the tissue wall. With the threaded instrument 210 advanced at least partially into the septal wall AS, a guidewire 17 or other instrument may be passed directly through threaded instrument 210 and into the left atrial chamber LA.

Figure 18A:
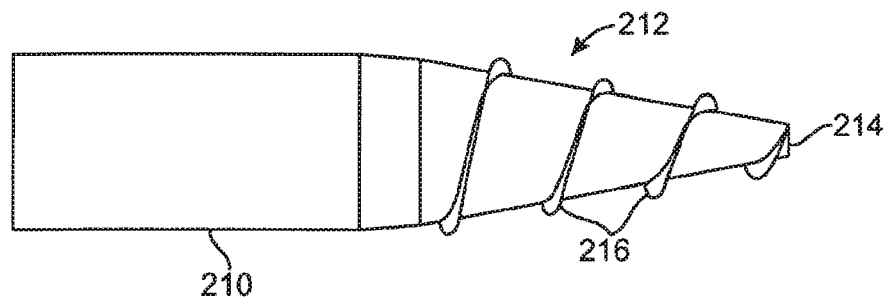
FIGS. 18A and 18B show side and cross-sectional side views, respectively, of a variation of a threaded engagement instrument defining a lumen therethrough.
Figure 18B:
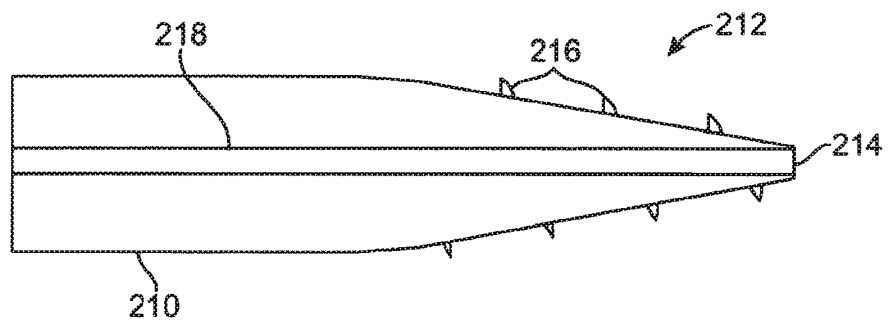
Figure 19A:
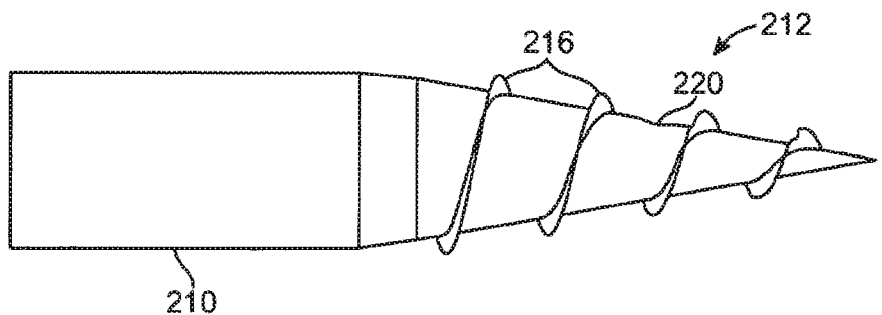
FIGS. 19A and 19B show side and cross-sectional side views, respectively, of another variation of a threaded engagement instrument defining a lumen opening along a side surface of the instrument.
Figure 19B:
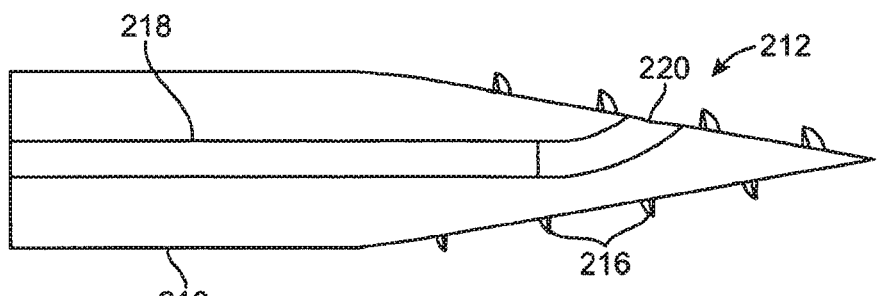

FIGS. 18A and 18B show detail side and cross-sectional side views, respectively, of one variation of a threaded engagement instrument defining a lumen 218 therethrough which may be utilized for passing into and/or through a tissue wall in a controlled manner while inhibiting or preventing tissue tenting. As shown, the distal end effector may be tapered with threads 216 defined thereupon with lumen 218 terminating with distal opening 214 through which any number of additional tools or instruments may be passed. FIGS. 19A and 19B detail show side and cross-sectional side views, respectively, of another variation of a threaded engagement instrument 210 defining a lumen opening 220 along a side surface of the instrument. In this variation, a instrument such as a guidewire may be passed through lumen 218 to exit through side opening 220 at an angle relative to instrument 210, if so desired. In either variation, the threading 216 may be variably pitched to improve its engagement and anchoring performance.

In yet other variations, threaded engagement instrument may be configured as a penetrating helical tissue engager through which a guidewire may be advanced. Such variations and other examples are described in further detail in U.S. patent application Ser. No. 11/763,399 filed Jun. 14, 2007, which is incorporated herein by reference in its entirety.

Figure 20A:
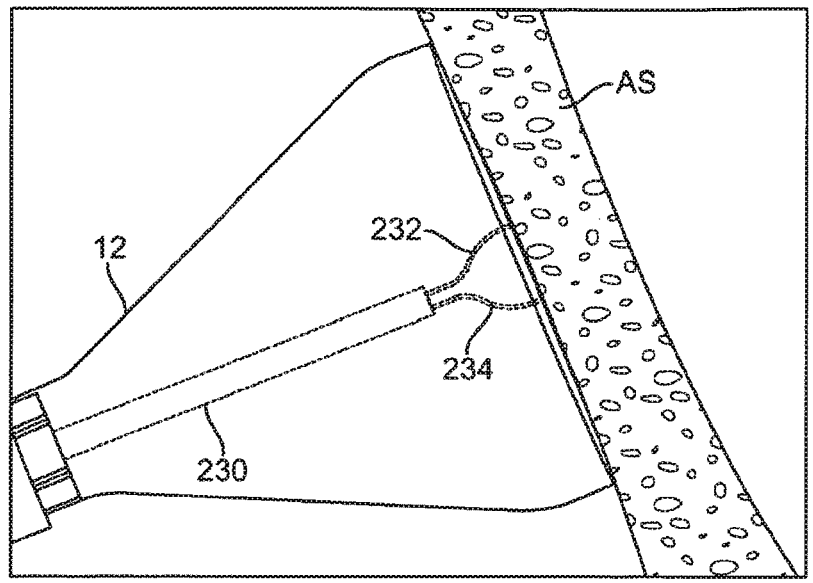
FIGS. 20A and 20B show side views of another instrument for temporarily grasping the underlying tissue wall with curved grasping elements to provide a counter-traction force by engaging the surface of the septum wall.
Figure 20B:
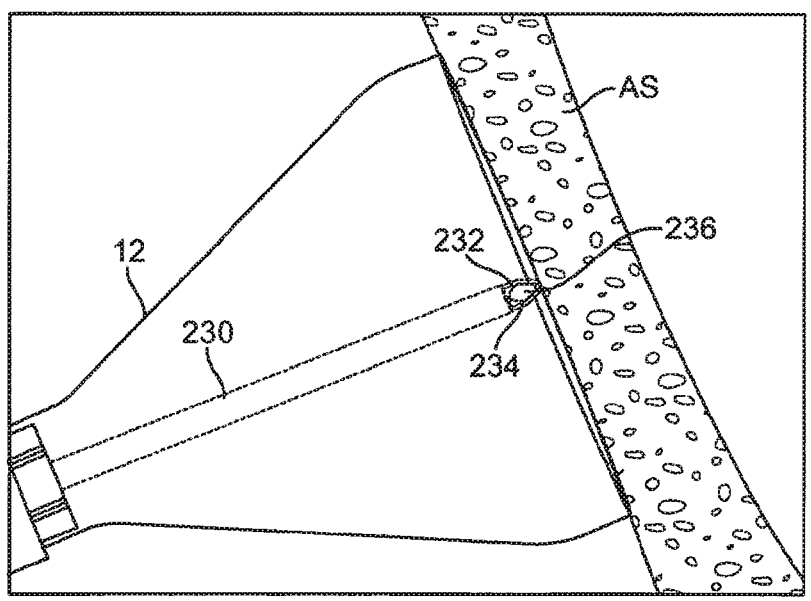

Another variation of an instrument for providing counter-traction is shown in the side views of FIGS. 20A and 20B. In this variation, at least two opposing grasping elements 232, 234 may be deployed from tubular member 230 for pinching and holding a portion of the underlying tissue. Grasping elements 232, 234 may be fabricated from a resilient material such as a shape memory alloy, e.g., Nickel-Titanium alloy, or spring stainless steel, etc. such that the elements 232, 234 are reconfigurable from a low profile delivery configuration when disposed within a lumen of tubular member 230 to an expanded tissue grasping configuration, as shown in FIG. 20A. When deployed and reconfigured within or distal to hood 12, elements 232, 234 may be advanced into or against the tissue surface. Once the tissue has been contacted, elements 232, 234 may be retracted into tubular member 230 or tubular member 230 may be advanced distally over elements 232, 234 such that the elements 232, 234 are forced to collapse towards one another while grasping and pinching a portion of tissue 236 therebetween, as shown in FIG. 20B.

Figure 21A:
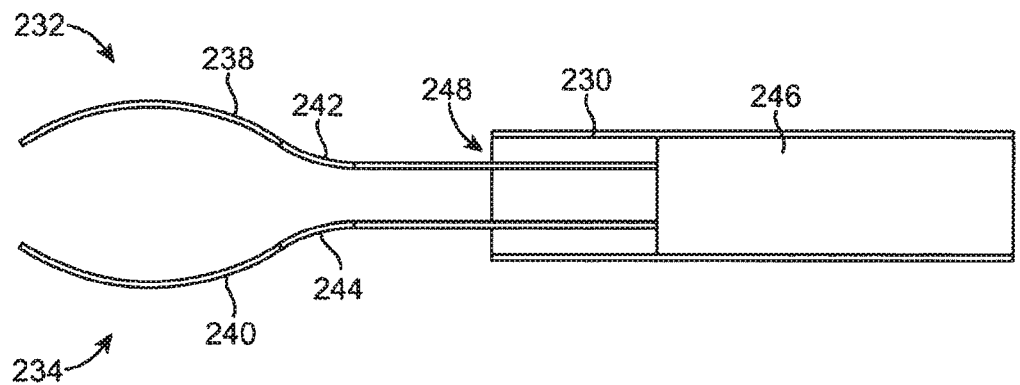
FIGS. 21A and 21B show side views of one variation of a counter-traction instrument having curved grasping elements which are reconfigurable between a low-profile configuration and a deployed configuration.
Figure 21B:
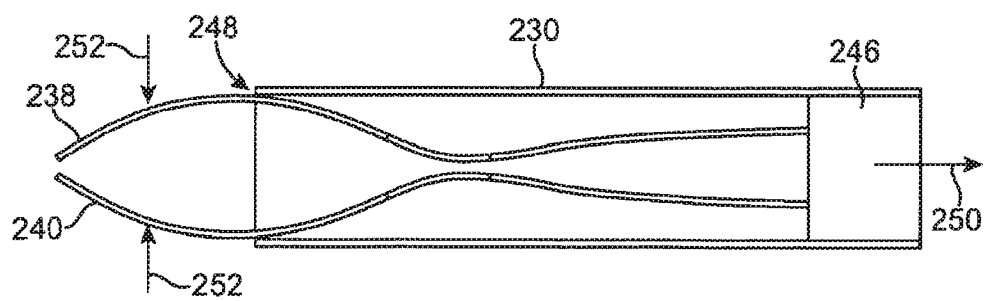

An example of a pinching engagement device may be seen in the partial cross-sectional views of FIGS. 21A and 21B. The counter-traction engagement device may utilize a pair of reconfigurable curved grasping elements 238, 240 which are connected via angled or curved portions 242, 244 to a support member 246. Curved grasping elements 238, 240 may be reconfigurable from a low-profile configuration to a deployed configuration and which may be controlled by sliding within lumen 248 relative to tubular member 230. When retracted in a proximal direction 250 from its deployed shape to its low-profile shape, the curved grasping elements 238, 240 may be drawn towards one another, as indicated by the direction of articulation 252, to force a pitching motion which may be utilized for temporarily pinching or holding the underlying tissue.

Figure 22A:
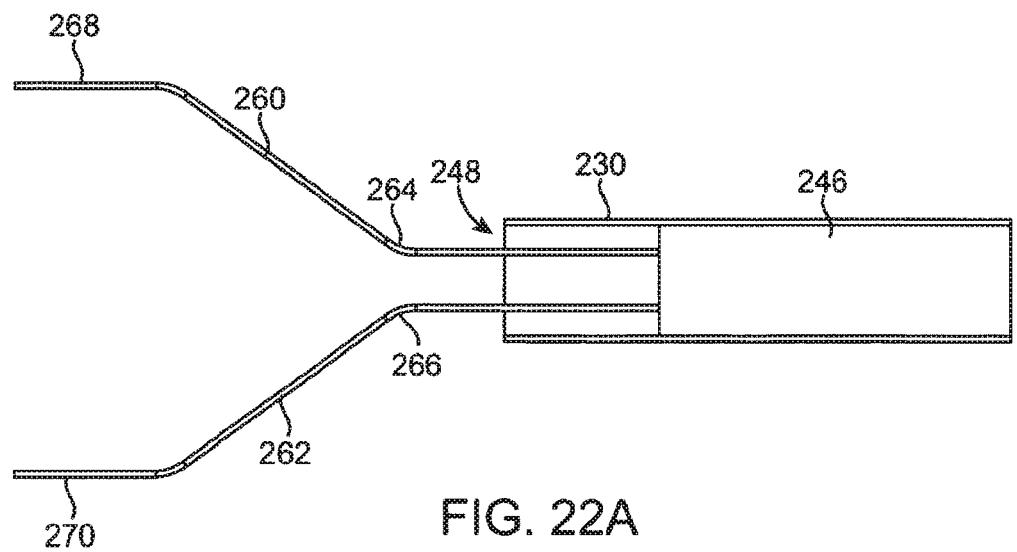
FIGS. 22A and 22B show side views of another variation of a counter-traction instrument having linearly projecting grasping elements.
Figure 22B:
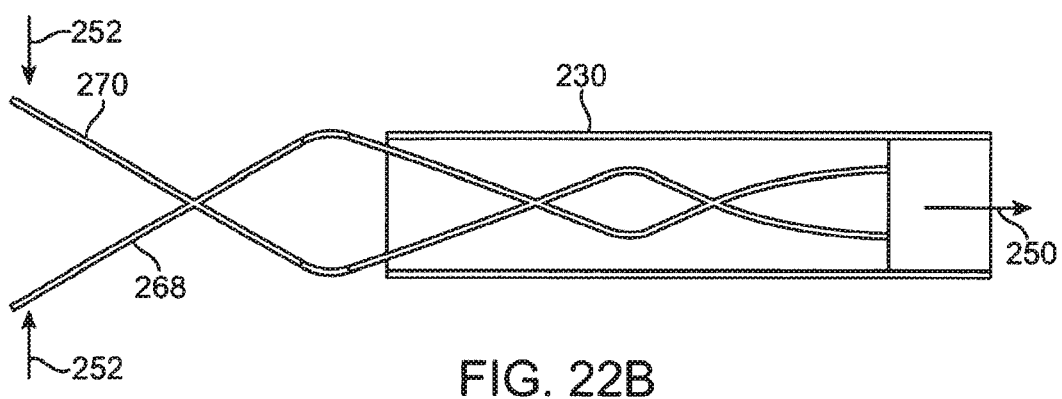

FIGS. 22A and 22B illustrate side views of another variation of a pinching or grasping instrument utilizing linearly projecting grasping elements 268, 270 connected via straightened linking members 260, 262 which are in turn connected to support member 246 via angled or curved portion 264, 266. As above, when support, member 246 is retracted proximally 250, the distal grasping element 268, 270 may be drawn towards one another, as indicated by the direction of articulation 252, to force a pitching motion.

Figure 23A:
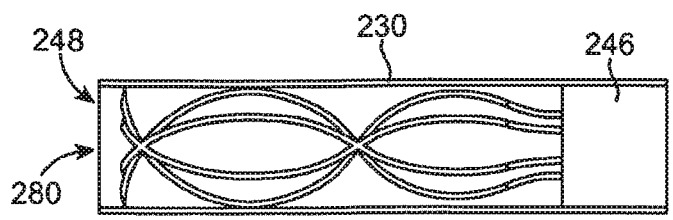
FIGS. 23A to 23C show side views of yet another counter-traction instrument fabricated from shape-memory materials which deploy from a low-profile configuration into a radially curved configuration for retaining tissue.
Figure 23B:
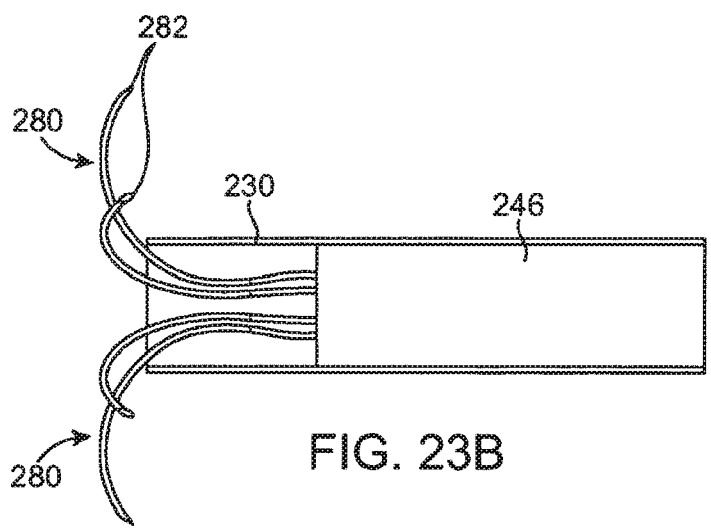
Figure 23C:
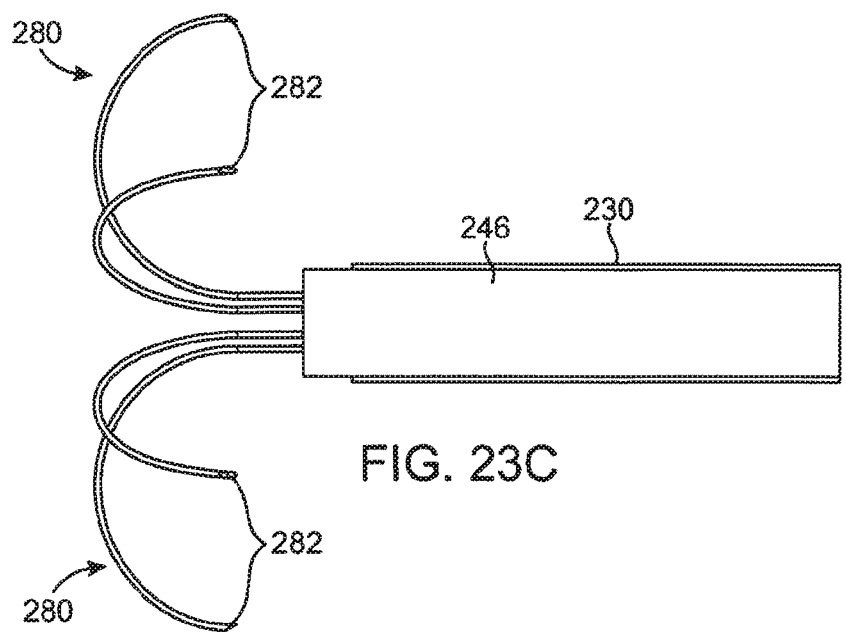
Figure 23D:
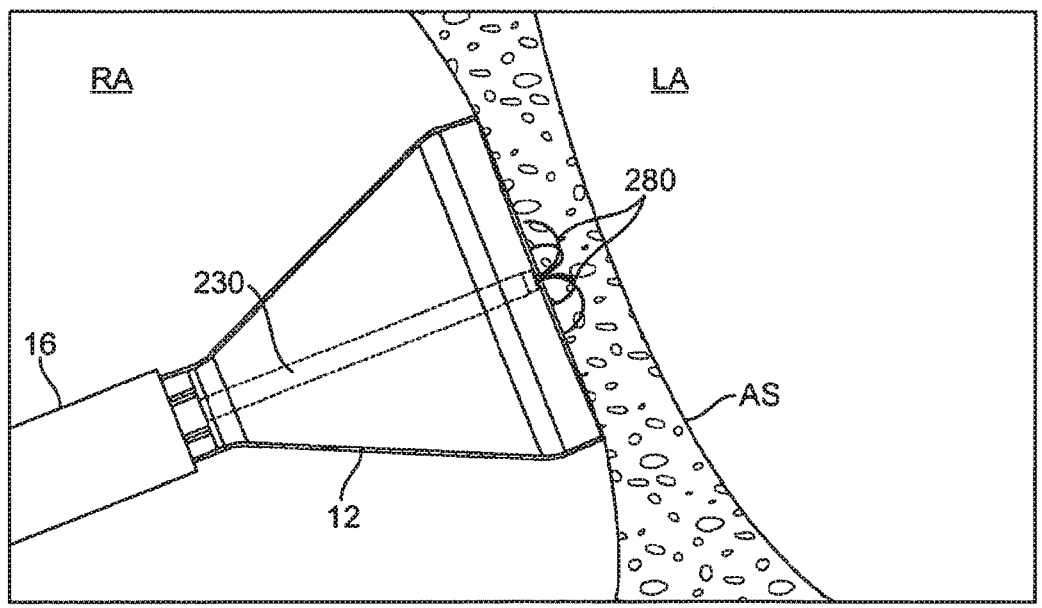
FIG. 23D shows a side view of the instrument of FIG. 23C deployed and engaged to the septum wall to provide a counter-traction force against "tenting" effects.

Another variation may utilize the grasping elements 280 fabricated from a shape memory alloy, such as Nickel-Titanium alloy, where activation of the shape memory alloy could be from heat, electricity, or other methods. The shape memory alloy could be the grasping element itself or it could be integrated as a part of a mechanism that facilitates engagement. FIG. 23A shows a variation where the shape memory alloy is configured into multiple grasping elements 280 each having a piercing tip 282 positioned within the tubular member 230. When support member 246 is advanced distally, the grasping elements 280 may be begin to expand radially, as shown in FIG. 23B, until elements 280 are fully expanded into its radially curved configuration, as shown in FIG. 23C. Each of the grasping elements 280 may curve proximally, much like a hook, to facilitate attachment to the tissue and to provide anchorage and a counter traction force to reduce and/or eliminate "tenting" effects. FIG. 23D illustrates an example where grasping elements 280 may be advanced and expanded into its deployment shape within the septal wall AS to temporarily retain the tissue. To release the tissue, elements 280 may be retracted by support member 246 such that they collapse back into their low profile configuration within tubular member 230.

Other examples of grasping elements may include any number of projections or elements, such as hooks, teeth, etc. Moreover, a single or a plurality of grasping elements may be utilized. The grasping elements may also be engaged or disengaged in a variety of different ways. By pulling proximally on the tissue towards the interior of hood 12, tenting of the tissue into the left atrium LA may be avoided when pushing distally with the piercing instrument upon the tissue wall. Moreover, by pulling proximally on the tissue, accidental puncturing of surrounding anatomical structures may be potentially avoided when passing needle or other instruments through the tissue by preventing or inhibiting tissue tenting, as described above. Further examples of grasping instruments are described in further detail in U.S. patent application Ser. No. 11/763,399, incorporated hereinabove.

Figure 24A:
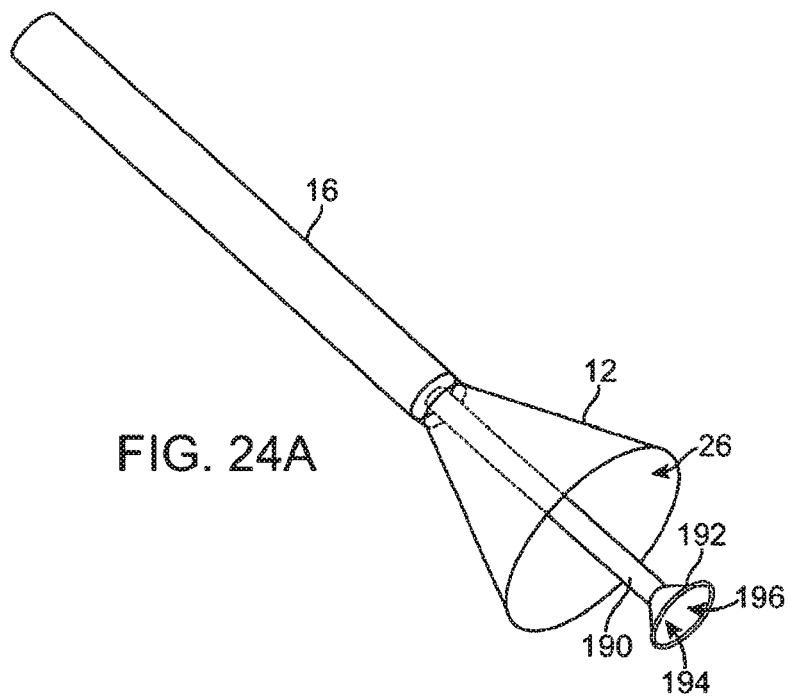
FIG. 24A shows a perspective view of an apparatus similar to that of FIG. 15A having a primary and secondary double hood configuration.
Figure 24B:
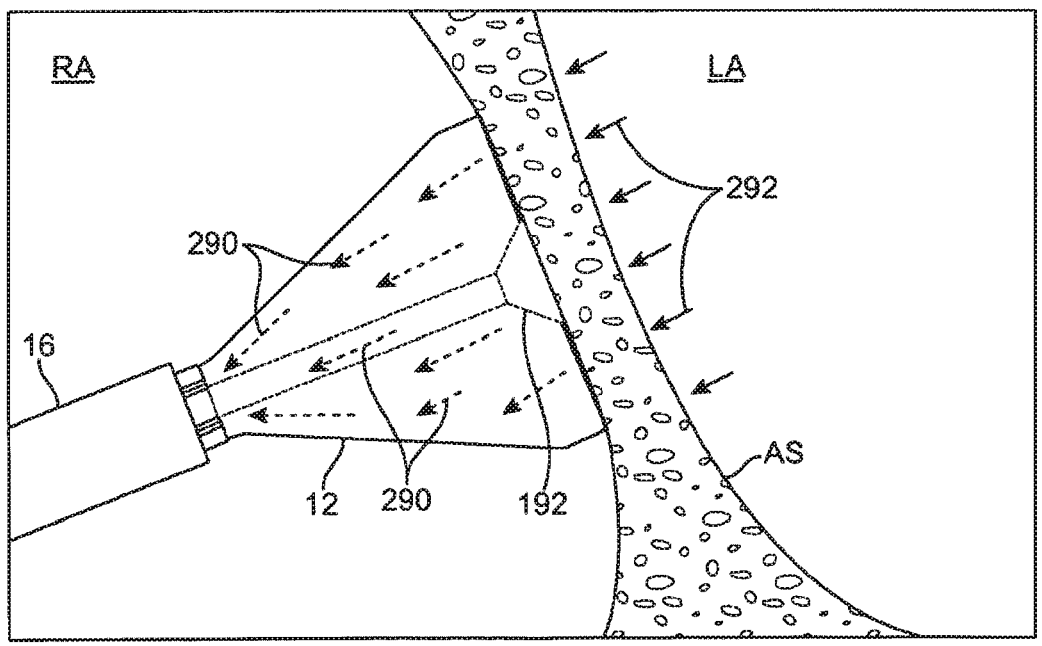
FIG. 24B shows a side view of the device of FIG. 24A providing negative pressure within the hood to prevent the septum wall from "tenting".

In yet another variation, as shown in FIGS. 24A and 24B, the tissue of the atrial septum AS can be engaged using a vacuum created within imaging hood 12. Initially, the imaging hood 12 may be deployed and the location for crossing the atrial septum AS determined using the imaging element and flushing port as described above. Once the location has been determined, the tissue may be engaged using a suction force within secondary hood 192 to draw in the approximated tissue and hold it securely within hood 12, as shown and described above. While the tissue is engaged using the vacuum, a needle can be passed through the atrial septum AS and into the left atrium LA. As described above, the needle 520 may pass a guidewire 17 therethrough across the atrial septum AS. By pulling proximally on the tissue, accidental puncturing of surrounding anatomical structures may be potentially avoided when passing needles or other instruments through the tissue by preventing or inhibiting tissue tenting, as further described in U.S. patent application Ser. No. 11/763,399 which is incorporated hereinabove.

Alternatively, the smaller secondary hood 192 may be utilized to pass tools (such as needles or guidewires, etc.) and/or to provide visualization (via CCD camera or fiberscope, etc.). Rather than drawing a vacuum within secondary hood 192, a negative pressure 290 may be created within hood 12 outside of secondary hood 192 to draw the tissue against the hood 12, as indicated by the direction of tissue apposition 292 in FIG. 24B.

Figure 25A:
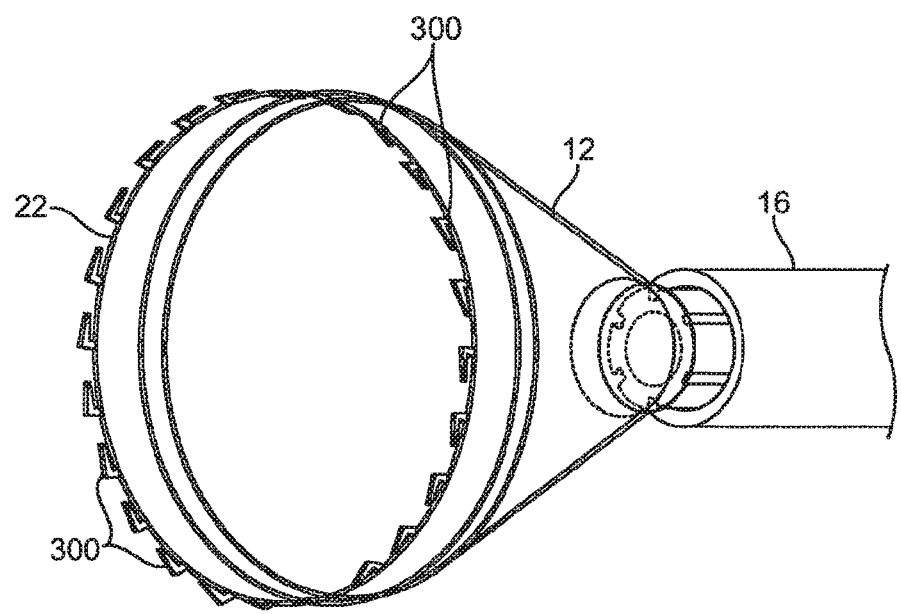
FIGS. 25A and 25B show perspective and side views, respectively, of another variation of the tissue visualization catheter having a plurality of angled teeth or pins, e.g., at right-angles, along a circumference of the hood.
Figure 25B:
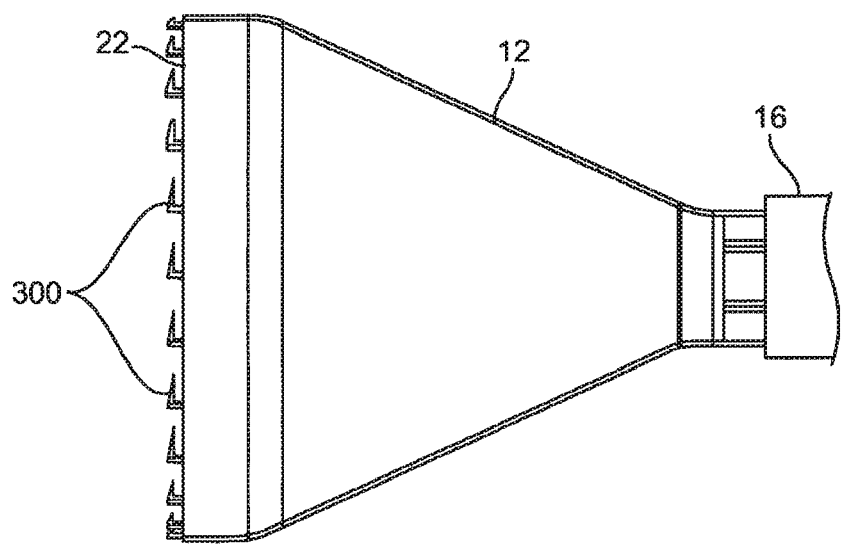

Aside from utilizing grasping instruments passed through hood 12 to create a counter-traction force during, e.g., a transseptal procedure, one or more projections or retaining members may be placed around a periphery of hood 12 itself, e.g., around a circumference of contact lip or edge 22. One such example is shown in the perspective and side views of FIGS. 25A and 25B, respectively, where hood 12 may include a plurality of rotationally engaging elements 300 oriented, e.g., at right angles relative to a longitudinal axis of the catheter 16. These elements 300 may be temporarily engaged onto the tissue by torquing hood 12 about its longitudinal axis such that these elements 300 are driven rotationally into the underlying tissue, as also illustrated above in FIG. 17. Engaging elements 300 may be fabricated from any number of biocompatible metallic or polymeric materials which are attached or otherwise integrated with hood 12.

Figure 26A:
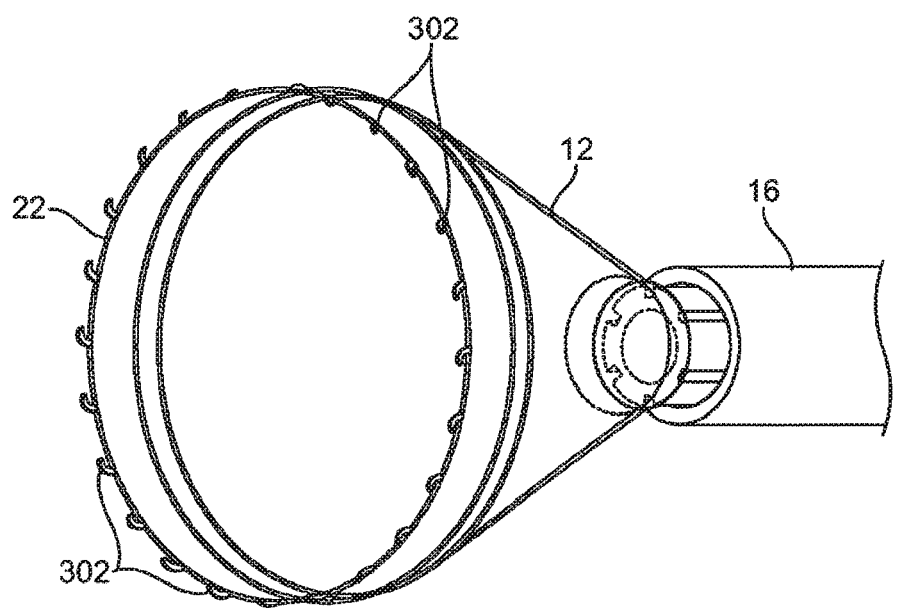
FIGS. 26A and 26B show perspective and side views, respectively, of another variation of the tissue visualization catheter having a plurality of hooks or barbs along the circumference of the hood.
Figure 26B:
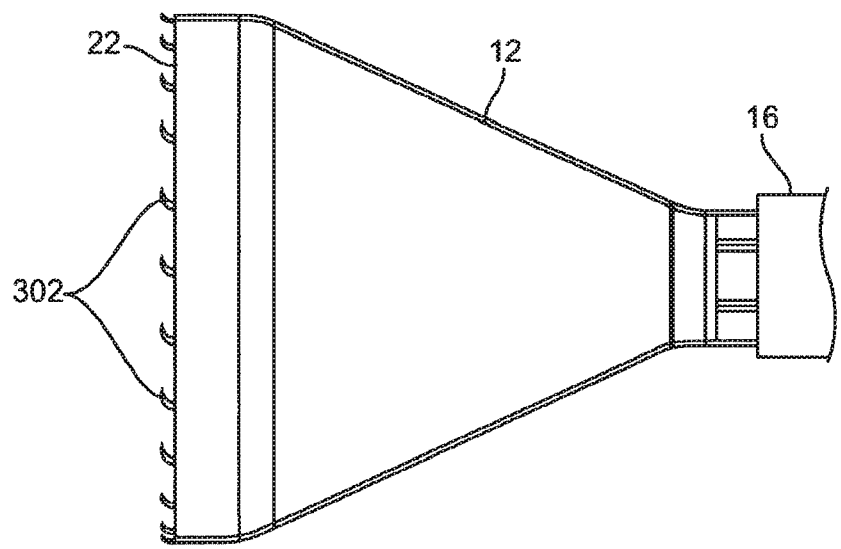
Figure 27A:
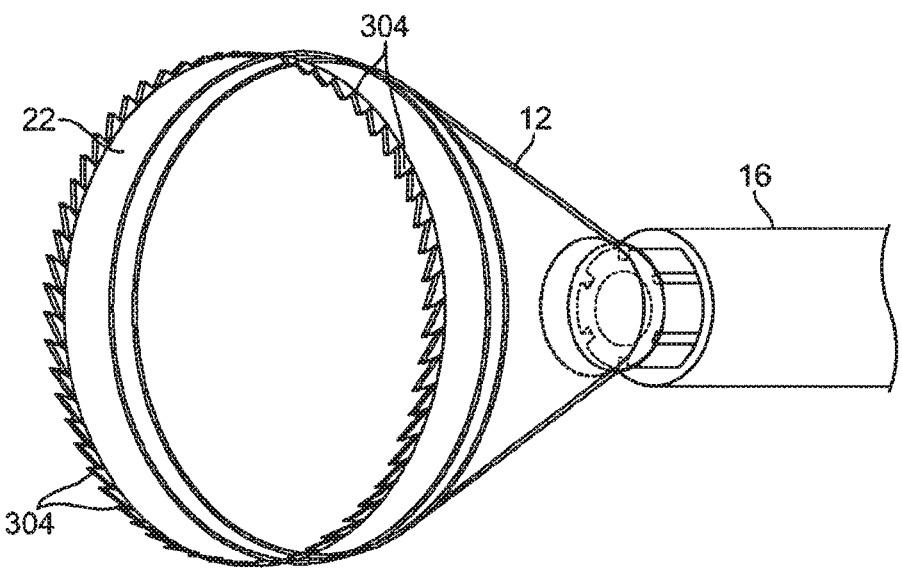
FIGS. 27A and 27B show perspective and side views, respectively, of yet another variation of the tissue visualization catheter having a plurality of jagged teeth along the circumference of the hood.
Figure 27B:
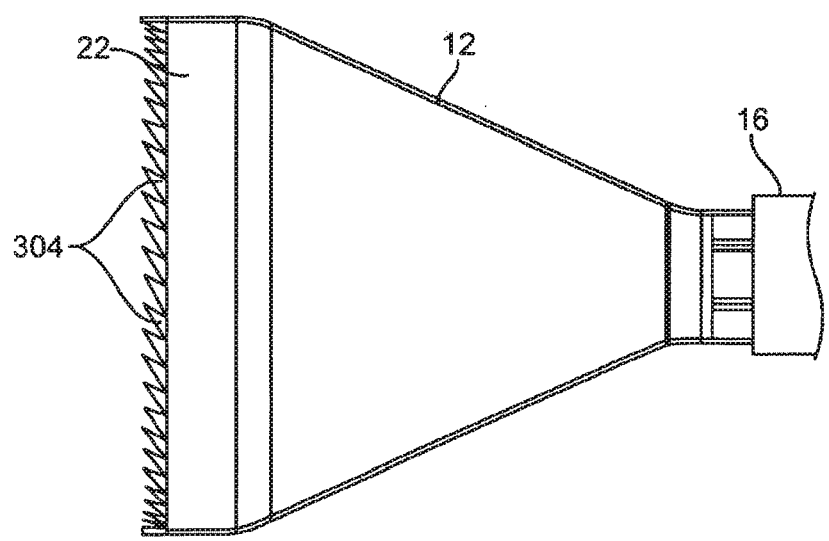

FIGS. 26A and 26B illustrate perspective and side views, respectively, of another variation utilizing a plurality of hooks or barbed elements 302 projecting from around the circumference of hood 12. FIGS. 27A and 27B show yet another alternative variation utilizing jagged teeth 304 around the rim of hood 12. The rotationally engaging elements could also be positioned along two separate circular elements that are counter rotated to engage against the tissue. The rotational element may also be locked into engagement against the tissue by extending anchors, such as straight pins attached along the circumference of the hood 12, that may be inserted into the tissue wall perpendicularly relative to the engaging teeth to prevent reverse rotation and disengagement from the tissue.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. An apparatus for inhibiting tissue migration during a procedure, comprising:
   a deployment catheter defining at least one lumen therethrough;
   a non-inflatable hood projecting distally from the deployment catheter and forming a boundary around an open area between the deployment catheter and a circumferential edge of the non-inflatable hood, wherein the open area is in fluid communication with the at least one lumen;
   a visualization element disposed within or along the non-inflatable hood for visualizing tissue adjacent to the open area; and a tissue piercing instrument slidably positioned through the catheter and the open area, the tissue piercing instrument including a tissue grasping end effector configured to temporarily engage the tissue adjacent to the open area, while the circumferential edge surrounding the tissue piercing instrument engages the tissue, such that distal migration of the tissue relative to the non-inflatable hood is inhibited, the end effector including a tapered section through which a lumen extends, the tapered section including threads fixedly extending from a surface of the tapered section in a direction orthogonal to a longitudinal axis of the catheter, wherein the lumen is configured to receive an elongated instrument after the tissue grasping end effector engages the tissue such that the tissue grasping end effector provides a counter-traction against the tissue as the elongated instrument advances through the lumen and into the tissue, and wherein the tissue grasping end effector comprises a secondary hood positioned slidably within the open area bounded by the non-inflatable hood and configured to adhere the tissue thereto via negative pressure within the secondary hood.

2. The apparatus of claim 1 wherein the non-inflatable hood comprises a conical hood bounded at a distal end by the circumferential edge.

3. The apparatus of claim 1 further comprising a plurality of projections extending distally from the circumferential edge of the non-inflatable hood where the projections are configured to engage tissue thereto.

4. The apparatus of claim 1 further comprising a plurality of radiopaque elements positioned along the non-inflatable hood.

5. The apparatus of claim 1 further comprising one or more flexible members slidably positioned through the open area, where each of the one or more flexible members comprise a radiopaque distal end.

6. An apparatus for inhibiting tissue migration during a procedure, comprising:
 a deployment catheter defining at least one lumen therethrough;
 a hood projecting distally from the deployment catheter and forming a boundary around an open area between the deployment catheter and a circumferential edge of the hood, wherein the open area is in fluid communication with the at least one lumen;
 a visualization element disposed within or along the hood for visualizing tissue adjacent to the open area; and
 a tissue piercing instrument extendable through the catheter and into the open area, the tissue piercing instrument including a threaded tissue engager configured to rotate into the tissue adjacent to the open area, while the circumferential edge surrounding the tissue piercing instrument engages the tissue, such that distal migration of the tissue relative to the hood is inhibited, the threaded tissue engager including a tapered section through which a lumen extends, the tapered section gradually decreasing in diameter towards a distal end of the catheter, wherein the lumen is configured to receive an elongated instrument after the threaded tissue engager engages the tissue such that the threaded tissue engager provides a counter-traction against the tissue as the elongated instrument advances through the lumen and into the tissue,
 wherein the tissue piercing instrument comprises a secondary hood positioned slidably within the open area bounded by the hood and configured to adhere the tissue thereto via negative pressure within the secondary hood.

7. The apparatus of claim 6 further comprising the elongated instrument, wherein the elongated instrument includes a guidewire slidably disposed through the lumen defined through the threaded tissue engager.

* * * * *